United States Patent [19]
Duffy

[11] Patent Number: 5,983,467
[45] Date of Patent: Nov. 16, 1999

[54] INTERLOCKING DEVICE

[76] Inventor: Leonard A. Duffy, P.O. Box 366, Hinesburg, Vt. 05461-0366

[21] Appl. No.: 08/999,521

[22] Filed: Dec. 29, 1997

Related U.S. Application Data

[60] Provisional application No. 60/034,096, Dec. 30, 1996.

[51] Int. Cl.$^6$ .................................................. A44B 18/00
[52] U.S. Cl. ............................. 24/442; 24/575; 24/452; 24/577; 403/381
[58] Field of Search ............................ 24/306, 442–452, 24/575, 576, 577; 403/331, 363, 335, 381

[56] References Cited

U.S. PATENT DOCUMENTS

| | | |
|---|---|---|
| 78,116 | 5/1868 | Moore . |
| 748,603 | 1/1904 | Henry . |
| 1,424,481 | 8/1922 | Isoardi . |
| 2,016,382 | 10/1935 | McBurney . |
| 2,074,928 | 3/1937 | Miller . |
| 2,596,995 | 5/1952 | Hamilton . |
| 2,717,437 | 9/1955 | De Mestral ................................ 28/72 |
| 2,774,121 | 12/1956 | Graevenitz et al. . |
| 3,050,124 | 4/1962 | Ottenbacher . |
| 3,101,517 | 8/1963 | Fox et al. ............................... 24/452 X |
| 3,192,589 | 7/1965 | Pearson .................................... 24/204 |
| 3,408,705 | 11/1968 | Kayser et al. ............................ 24/204 |
| 3,484,907 | 12/1969 | Elsenheimer ............................. 24/206 |
| 3,785,003 | 1/1974 | Thomson ................................ 16/87.2 |
| 3,921,259 | 11/1975 | Burnlik .................................... 24/204 |
| 4,019,298 | 4/1977 | Johnson, IV ............................. 52/594 |
| 4,183,121 | 1/1980 | Cousins .................................... 24/204 |
| 4,581,792 | 4/1986 | Spier ........................................ 24/575 |
| 4,610,100 | 9/1986 | Rhodes ....................................... 36/42 |
| 4,670,960 | 6/1987 | Provost ................................ 24/442 X |
| 5,208,952 | 5/1993 | Mintel et al. ......................... 24/575 X |
| 5,212,855 | 5/1993 | McGanty ............................... 24/452 X |
| 5,269,776 | 12/1993 | Lancaster et al. ....................... 604/387 |
| 5,396,963 | 3/1995 | Curry .................................. 403/381 X |
| 5,425,524 | 6/1995 | Messina, Jr. ......................... 248/475.1 |
| 5,447,772 | 9/1995 | Flieger ................................. 24/576 X |
| 5,596,794 | 1/1997 | Shibanushi ............................... 24/452 |
| 5,607,635 | 3/1997 | Melbye et al. .......................... 264/169 |
| 5,625,929 | 5/1997 | Hattori et al. ............................ 24/452 |
| 5,640,744 | 6/1997 | Allan ........................................ 24/442 |
| 5,657,516 | 8/1997 | Berg et al. ............................... 24/452 |

FOREIGN PATENT DOCUMENTS

| | | | |
|---|---|---|---|
| 298117 | 7/1964 | Switzerland ............................. 24/577 |
| 760697 | 11/1956 | United Kingdom .................... 24/577 |
| 963948 | 7/1964 | United Kingdom .................... 24/577 |

Primary Examiner—James R. Brittain
Assistant Examiner—Robert J. Sandy

[57] ABSTRACT

Two portions are joined by a set of islands provided on one surface engaged within apertures provided on a second surface, said islands being configured so as to provide apertures between sets of adjacent islands so that, when the assembly is subjected to a relative shearing force, the islands may be engaged by complementary apertures thus forming a secure union which may be readily disconnected and reconnected, is adjustable, and which is useful as a fastener for diverse rigid or flexible materials. Also provided are alternate shapes and configurations of the device, diverse means for coupling the assembly in pre-engaged and engaged position, embodiments which may also provide a reusable seal, embodiments which may provide an electrical connector, and other variations, The device may be furnished as a singular set, in a linear plurality, in a two dimensional array, as a plurality which connects two coplanar parts by connection with a third part, and other designs.

61 Claims, 10 Drawing Sheets

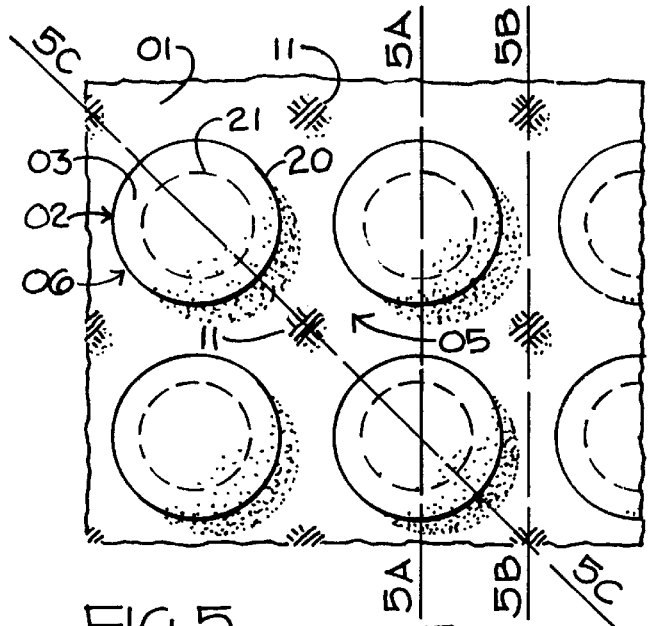
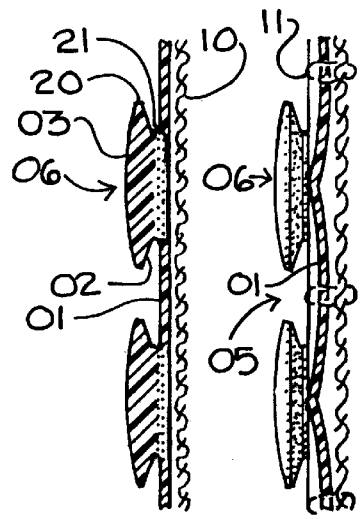
FIG. 5   FIG.5A  FIG.5B
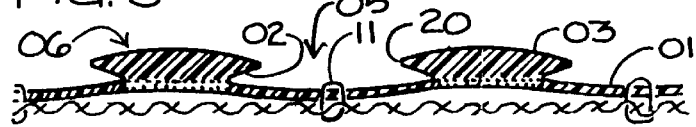
FIG. 5C
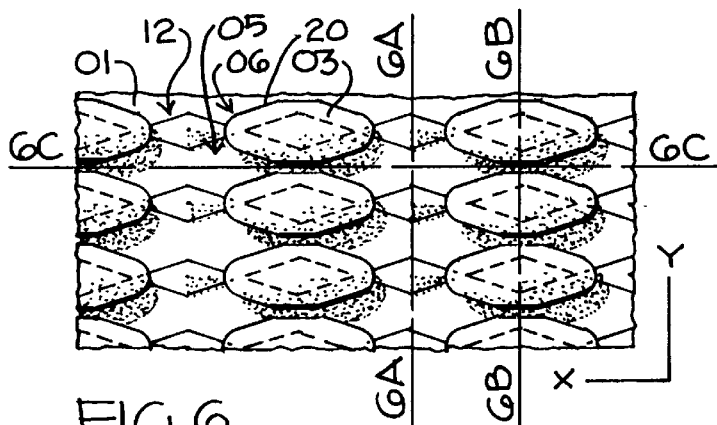
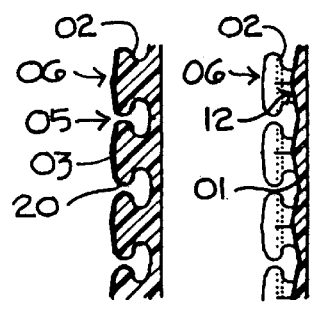
FIG. 6   FIG.6A  FIG.6B
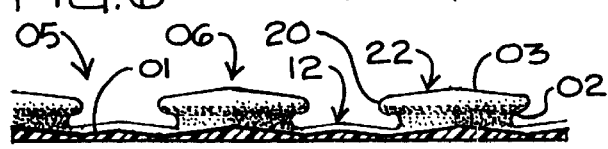
FIG. 6C

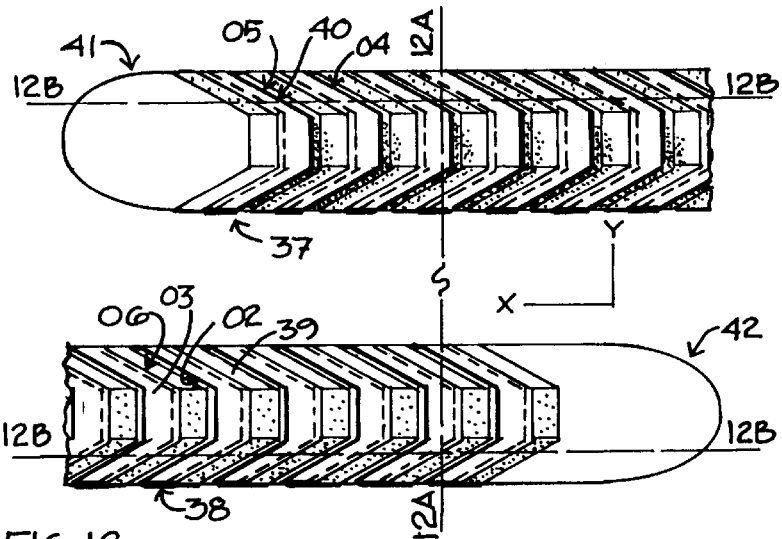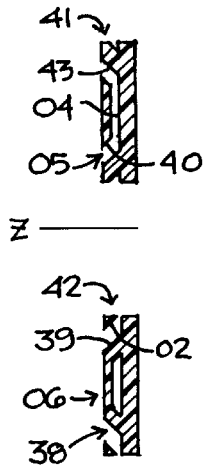
FIG.12  FIG.12A
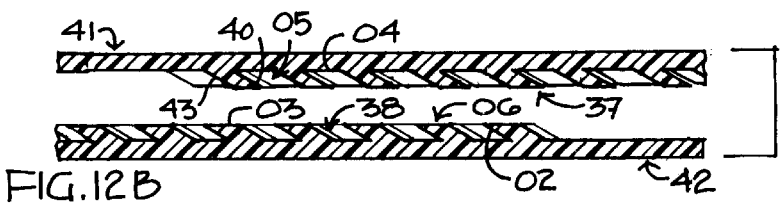
FIG.12B
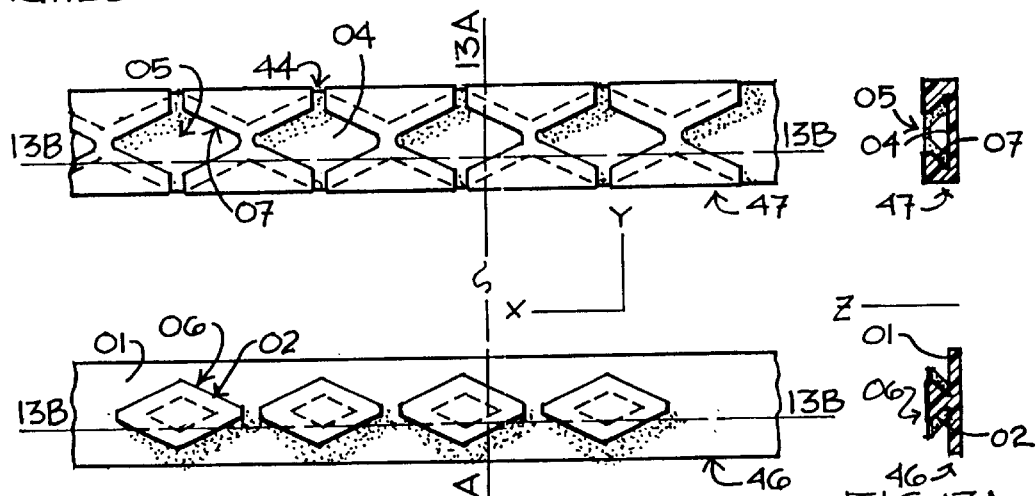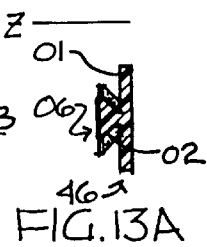
FIG.13  FIG.13A
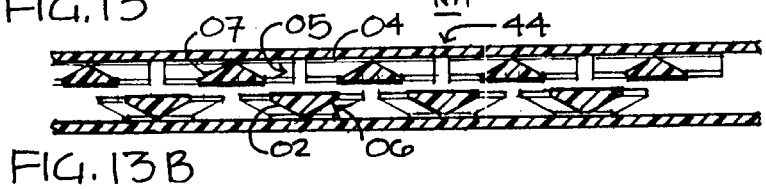
FIG.13B

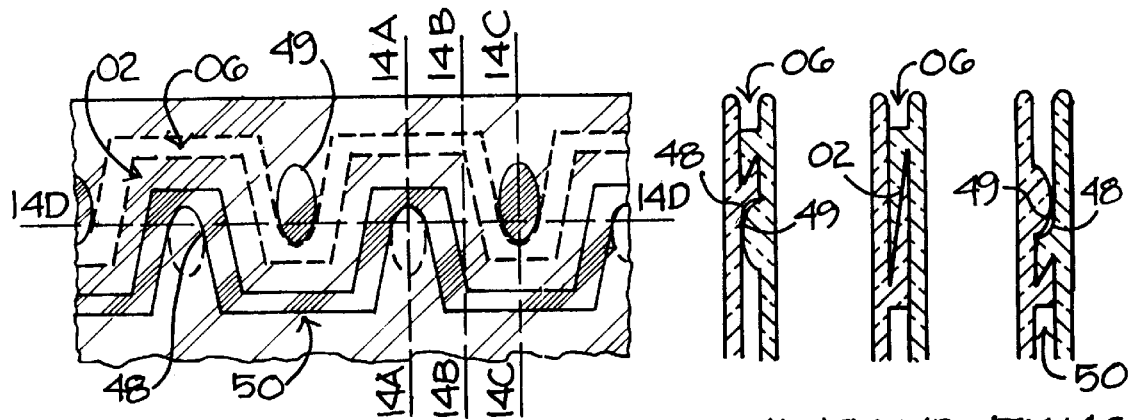
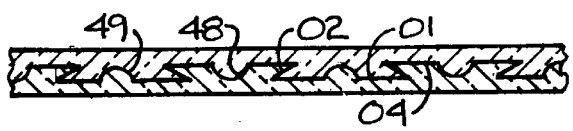
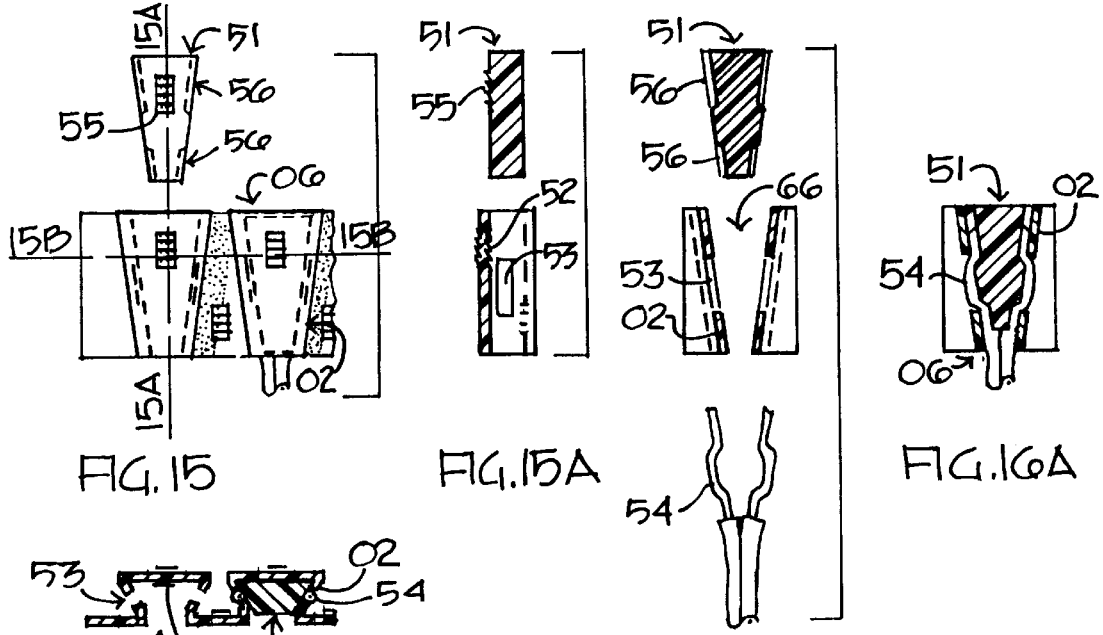
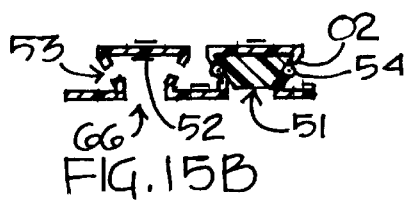

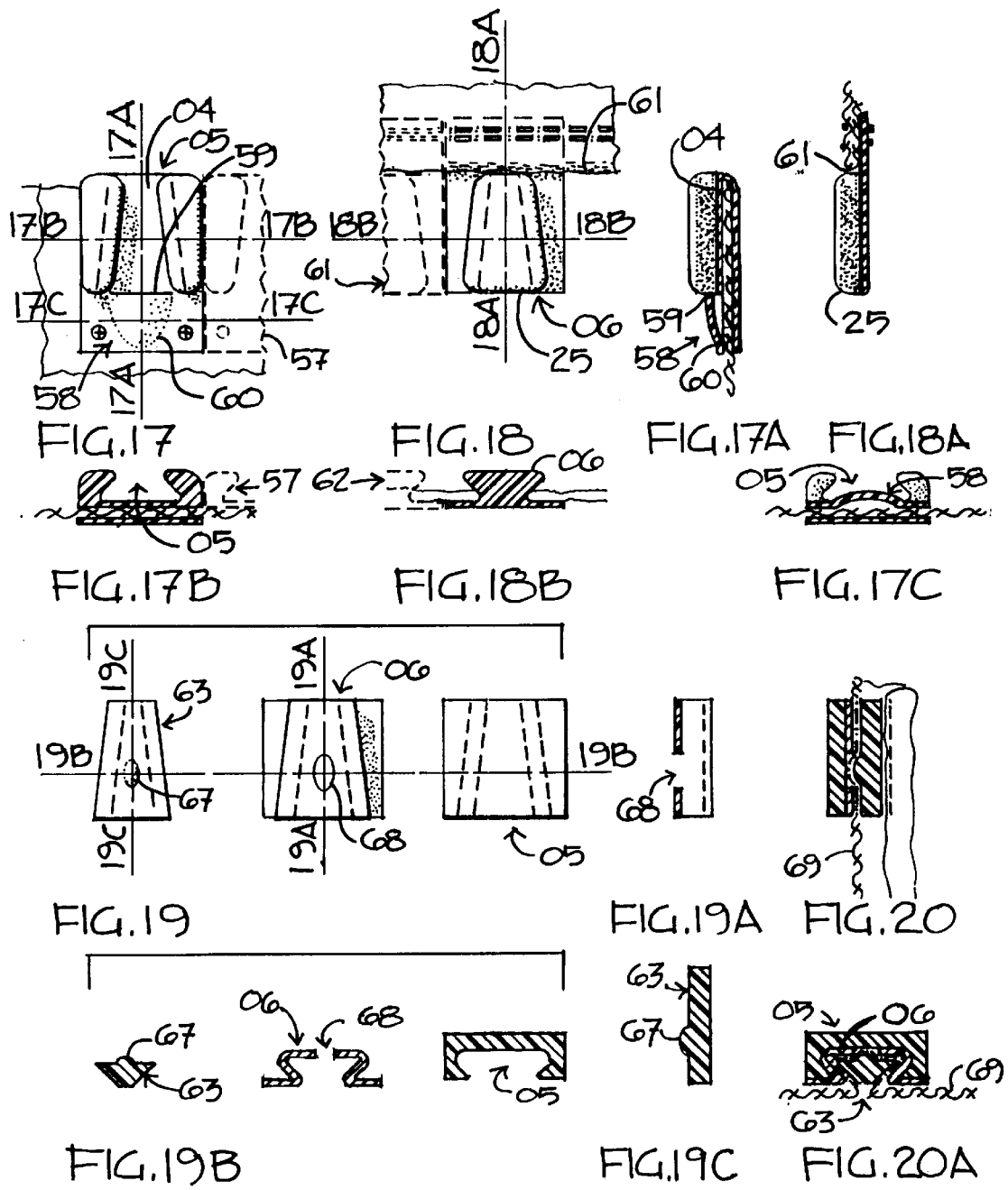

INTERLOCKING DEVICE

This Appln claims benefit of Provisional appln No. 60/034,096 Dec. 30, 1996.

BACKGROUND

1. Field of the Invention

The present invention is related to mechanical fastening devices, in particular those used for connecting a wide variety of rigid or flexible materials.

2. Prior Art

Devices which interconnect two surfaces by use of interdigitated parts are known. Also known are devices which effect a connection by means of a doubly tapered wedge inserted into a similarly shaped aperture.

Slide fasteners, hook and loop devices, other press together systems, and various forms of interlocking longitudinal shapes such as those used in plastic food storage bags are commonly utilized for attaching flexible materials. Certain of these devices may provide for lineal adjustability. Rigid materials are sometimes connected by interdigitated mortises and tennons and various types of interlocking joints, such as the dovetail joint common to woodworking.

In regard to fastening flexible materials such as apparel, fabric, leather, rubber, plastics, or other flexible sheet goods the zipper is probably the most common means in use today. The zipper has considerable merit as a quick, relatively secure fastening device which can be readily detached, but it also has several disadvantages. The minimal surface area which actually acts against tensile forces can be over stressed causing failure. Extraneous materials such as hair or nearby fabric can readily jamb the fastener. Once jammed or broken the zipper is often rendered dysfunctional over its entire length and usually must be wholly replaced. The necessity of a sliding connector and its gripping device adds bulk and directionality to the overall unit which can be a negative aesthetic or functional consideration in many applications. It is not self-concealing thereby normally necessitating a covering flap or hem. The zipper requires directional attachment starting only at a connected end. A degree of manual dexterity is required which may be a disadvantage for people with certain disabilities as well as for those wearing gloves. For most applications it can not readily be made of plastic or other inexpensive low strength materials, and a highly precise capital intensive manufacturing system is necessary.

Hook and loop systems such as those produced under the tradename VELCRO, generally emanating from U.S. Pat. No. 2,717,437 to Mestral, are another common fastening method with considerable utility which are commonly used to connect flexible materials. Hook and loop systems also have several significant disadvantages. The force necessary to effect disengagement is directly related to the strength of the connection thereby limiting potential strength and at the same time requiring excessive force to effect disconnection. Precise register of the connection is difficult to achieve. The device is essentially designed to resist uplifting stresses although it is most commonly employed to resist stresses normal to the connected surfaces. Unintended foreign materials are easily attracted. Cleaning is difficult. Repetitive washing and/or use tends to weaken the connecting fibers. Strength is at least in part related to the profile thickness thereby frequently resulting in a bulky appearance. The texture of the exposed surface may cause discomfort or skin irritation. Specialized manufacturing methods are required and material choices are limited. In addition to the above, many people find both the exposed texture and the sound of disengagement to be objectionable.

Other systems of interconnecting shapes have also been developed and improved such as interlocking hermaphroditic "mushroom"-like projections, as per U.S. Pat. No. 3,192,589 to Pearson, which are pressed into each other so that the head of one such member is contained within the complementary heads and stems of a plurality of its counterparts. Vertical detachment is resisted by partial contact of the opposing under-surfaces. The base and/or the projection must be of sufficient resilience to allow insertion and removal. A recent example is U.S. Pat. No. 5,625,929 to Hattori which recognizes the inherent problem of such systems in resistance to horizontal shear and presents a means of limiting lateral slippage in a mushroom type fastener by providing a geometric pattern to the projections. These devices generally share many of the same disadvantages as hook and loop connectors, as stated above, in particular the direct relationship of strength to the force necessary for disconnection.

Several devices are presented in U.S. Pat. No. 5,269,776 to Lancaster and Young, for the purpose of fastening a disposable diaper, which utilizes a system of arrayed digits and apertures. Although it appears that this device will resist lateral stress via shear along the adjacent surfaces it is apparent that the digits of such a system will also tend to deform and release when a certain level of stress is applied. Again, the lateral stress resistance is related to the available release force. A similar concept is presented in U.S. Pat. No. 5,447,772 to Flieger.

It can be seen that a common characteristic of most of these "press together" devices is that they are primarily dependent on the tensile strength of the connecting elements to resist stresses both perpendicular and normal to the surface, more or less equally. Therefore, when sheared laterally, i.e. normal to the surface, the engaged elements tend to bend and align axially toward the direction of stress until failure is initiated by the release of a single connecting set. Since they are designed to primarily resist vertical tensile stresses, such devices are inherently limited in strength by the force necessary to voluntarily disengage the connection. Therefore, resistance to lateral stress, necessary release force, and failure stress are inherently related, a characteristic that can only be compensated for by substantially increasing the area of contact and actuating release by a peeling motion. Hook and loop systems, mushroom, and similar devices also generally tend to require a thickness which is at least partly proportional to strength. Therefore, a fastener offering reasonable strength generally must be relatively thick in profile: an aesthetic or functional disadvantage in many applications.

It will be recognized that in many, perhaps most, common applications of these devices horizontal shear stress on the assembly is predominant—not vertical tension. This is true, for instance, where such a device is used to close a shoe or jacket, in belt or band applications, or wherever the primary stress on a joint is normal to the surfaces to be connected. Therefore, in such applications, the integrity of the connection is typically limited by the necessity to provide relatively easy detachment—and the force necessary to achieve detachment is typically greater than that warranted for the use. Such systems are not inherently resistant to shear stresses and generally tend to deform and weaken rather than form a tighter bond when such stresses are applied.

Several other existent devices allow for lineal adjustment between overlapping surfaces. U. S. Pat. No. 3,484,907 to Elsenheimer describes several methods of effecting an adjustable fastener, one embodiment of which utilizes offset pairs of male/female shapes which are dovetail in profile and rectangular in plan. In this case lateral resistance is effected by the stop at the end of a slotted chamber and adjustment is effected by bypassing one surface to another set of male and female connectors. More recently U.S. Pat. No. 5,640,744 and others to Allan disclose adjustable straps utilizing interdigitated sloped links or teeth within a track which appears to be reasonably resistant to one-directional shear stress.

Numerous types of single point fasteners have been developed over time, the most common of which is the button. Other devices such as the snap fastener, various forms of buckles and hook and eye systems generally tend to have limitations as to their utility. Buttons and buckles are generally highly visible. Most of these systems provide one dimensional connection but allow lateral rotation. Though generally proven useful for particular applications each tends to have certain disadvantages which may limit utility. U.S. Pat. No. 78,116 to Moore describes a two piece "button" which interconnects by means of a compound dovetail and wedge and also includes a latching mechanism. By wedging the male structure into a receiving shape a fixed connection is effected which appears to resist shear. However, the male and female parts are not interchangeable, the male member has no base to provide rigidity, the device tends to rotate vertically when stressed, and the invention generally suffers from an attempt to appear like a common button. It appears to have little or no advantage over snap-type fasteners later developed.

Continuous interlocking spline joint systems, as for instance those commonly used for plastic food storage bags are useful for many applications, but also have certain disadvantages. Precise alignment and manual dexterity are required to obtain closure. Opening and reuse can be problematic. It is generally difficult to ascertain whether a seal has been effected. Strength is limited, applications are limited, and material and manufacturing methods are limited.

In regard to connecting rigid or semi rigid materials such as wood, sheet or structural metals, plastics, stone, etc. several methods exist which utilize interdigitated or singular oblique meeting surfaces. The "dovetail joint", for instance, is commonly used in woodworking and has sometimes been adopted for use with other materials. Typically the interdigitated dovetail is used as a method for permanently attaching planar materials at a right angle. By interconnecting a series of like shapes which are wider at one extremity than the other an effective joint is created which resists considerable stress. This type of joint is normally incised through the thickness of each joining member and must be used in conjunction with an adhesive on the contacting surfaces or some type of mechanical locking device in order to resist detachment. In a planar condition a dovetail connection with open faces would tend to slide apart unless fixed in place by other means. Several U.S. Patents have been issued for various improvements to such devices such as U.S. Pat. No. 435,759 to Marter but all appear to be related to a right angle connection, and generally employ unequal parts.

Singular sets of tapered dovetail and wedge connectors have been utilized for a several devices. U.S. Pat. No. 3,050,124 to Ottenbacher describes a pitless well adapter in which a waterproof joint is effected by gravitational pressure applied to such a device. U.S. Pat. No. 4,019,298 to Johnson utilizes a similar mechanism to effect a beam suspension system, also dependent on gravity, as well as a means of maintaining engagement utilizing a linear detent and corespondent depression on the sloped sides of the dovetail. More recently, U.S. Pat. No. 5,425,524 to Messina describes a leveling and guiding device for hanging objects which includes triangular members having a "dovetail" profile. In these and several other previously patented devices a connection is described between two unlike parts, male and female, typically singular sets dependent on gravity, which are utilized to effect a fixed structural condition. In general, such devices have been designed to align and/or join two specific male and female parts and are neither presented nor claimed as a generic multipurpose interlocking device. None are proposed for use in a plural or hermaphroditic configuration and none provide multi-directional fastening capabilities.

Various devices have been utilized to provide an electrical connector, generally including a plurality of male pins inserted into a plurality of female receptacles. Generally these devices are prone to disconnection when tension is applied and the pins are often subject to mechanical damage.

It can be seen from the foregoing that, based of the numerous systems presently available, there is a need for an interlocking device which provides simplicity, functional strength unrelated to the force necessary for disconnection, means of maintaining engagement, self alignment, minimal visibility, ease of manufacture, multiplicity of function, and diverse other advantages.

SUMMARY AND OBJECTS OF THE INVENTION

The present invention provides an interlocking device which is generally effectuated by one or more islands on the surface of a first portion which, when a relative shearing force is applied, slidingly engage one or more complementary apertures within a structure on the surface of a second portion. Said apertures are generally formed with sidewalls tapering in two perpendicular axes so as to retain said islands in a fixed position when the portions are fully engaged. Adjacent islands on one portion may be configured so as to form complementary apertures between their sidewalls and the basal surface, thus providing the option of a hermaphroditic assembly. Also furnished are diverse optional means of coupling or locking the assembly in its engaged position as well as in a pre-engaged position. Embodiments may be furnished which provide resistance to stresses in a single or multiple directions, which may be adjustable, which may effect a sealed connection, which may provide an electrical connection, which may connect two portions with a third, which may connect a single point, and which may provide numerous other functions.

The primary object of this invention is to provide an interlocking device, slidingly engaged by application of a relative shearing force, which is resistant to further shearing stresses and which, when so engaged, is also resistant to other stresses.

A second object is to provide such an interlocking device with means of coupling the portions in an engaged position.

Another object is to provide an interlocking device having means to retain the portions in a pre-engaged position resistant to disconnection.

Another object is to provide an interlocking device which may be furnished in an hermaphroditic configuration.

Another object is to provide an interlocking device which may be configured so as to resist shearing stresses in multiple directions.

Another object is to provide an interlocking device which is linearly adjustable and self aligning.

Another object is to provide an interlocking device providing a singular lockable connection resistant to shearing stress.

Another object is to provide an interlocking device which provides an electrical connection.

Another object is to provide an interlocking device which effects a sealed condition.

Other objects of this invention will become apparent throughout this disclosure.

In general the present device provides a simple, structurally sound connection which is easy to operate, which may be readily manufactured of a wide range of materials, and which may be varied in design to meet specific aesthetic or functional constraints. In its various embodiments it may be provided to connect flexible materials, rigid materials, or a rigid to a flexible material.

In comparison with other devices commonly used for connecting two portions, the present invention provides numerous advantages. The device provides significant resistance to shear stresses without requiring excessive effort to effect disconnection when desired. It is virtually jambproof. It does not require an extraneous moving part to effect closure. It is self concealing and presents minimal visibility where a flat surface is desired. It is easy to operate without requiring excessive manual dexterity. It is closeable from any point. It will continue to essentially function even with some elements missing or disconnected. It can effect more exacting register. It is not readily attracted to extraneous materials or surfaces. It can be readily cleanable without wearing out or weakening over time. Surface texture is not abrasive and will generally remain clean. Operation is noiseless. As an electrical connector advantages of such a device over existing technology include simplicity, security of connection, and protection of the contacting surfaces. And, the device can be produced in a variety of shapes, colors, sizes and materials for both aesthetic effect and manufacturing economy.

It is to be understood that this description is illustrative only and that considerable variation in the design, form, proportion, material, means of manufacture, applications as well as other aspects of the invention discussed herein may occur without departing from the scope of the invention.

SUMMARY OF THE DRAWINGS

The present invention is illustrated schematically in the following drawings which are intended to demonstrate a wide range of possible embodiments and combinations thereof. Each embodiment therefore illustrates certain aspects of the invention which may be combined in diverse configurations with those illustrated in other embodiments.

FIG. 5 is a plan view of one portion of an embodiment of the interlocking device incorporating a circular design well as another coupling means which may also attach the device to a substrate material.

FIGS. 5A–C are sectional views of the embodiment of FIG. 5.

FIG. 6 is a plan view illustrating a portion of an embodiment designed to resist tensile stresses primarily from two opposite axial directions, as well as another means of coupling.

FIGS. 6A–C are sectional views of the embodiment of FIG. 6.

FIG. 12 is a plan view of the two portions of a linearly adjustable embodiment of the interlocking device configured as at the ends of strap or band.

FIG. 12A is a sectional view of the embodiment shown in FIG. 12.

FIG. 12B is an exploded sectional view of the two portions of FIG. 12 each rotated ninety degrees into a pre-assembly alignment.

FIG. 13 is a plan view of the two portions of another linearly adjustable embodiment providing two directional stress resistance.

FIG. 13A is a sectional view of the embodiment of FIG. 13.

FIG. 13B is an exploded sectional view of the two portions of FIG. 13, each rotated ninety degrees into a pre-assembly alignment.

FIG. 14 is a plan view of an embodiment in which a plurality is laterally enjoined so as to effect a continuous connection which may form a seal, as in a pouch or bag, as well as a means of coupling the assembly and engaging the seal.

FIGS. 14A–D are sectional views of the embodiment of FIG. 14.

FIG. 15 is an exploded plan view of one portion of an embodiment of the interlocking device, partially assembled, that forms a connection and which may also connect an electrical circuit, as well as yet another coupling means.

FIGS. 15A–B are sectional views of the embodiment of FIG. 15.

FIGS. 16, 16A are sectional views of a singular unit of the embodiment of FIG. 15 illustrating an unassembled and assembled condition, respectively.

FIG. 17 is a plan view of one portion of an embodiment of the device as a singular fastening unit as well as a locking means.

FIGS. 17A–C are sectional views of the embodiment of FIG. 17.

FIG. 18 is a plan view of one portion of an embodiment compatible with that of FIG. 17 which also illustrates yet another means of coupling the assembly and attaching to a flexible substrate material.

FIGS. 18A–B are sectional views of the embodiment shown in FIG. 18.

FIG. 19 is a plan view of the three parts of one portion of an embodiment which provides a means of directly connecting a fabric or other flexible material to a singular unit of the device, as well as another means of coupling.

FIGS. 19A–C are sectional views of the embodiment of FIG. 19.

FIGS. 20, 20A are sectional views of the embodiment of FIG. 19 in an assembled condition.

DESCRIPTION OF THE INVENTION

Figure 1:
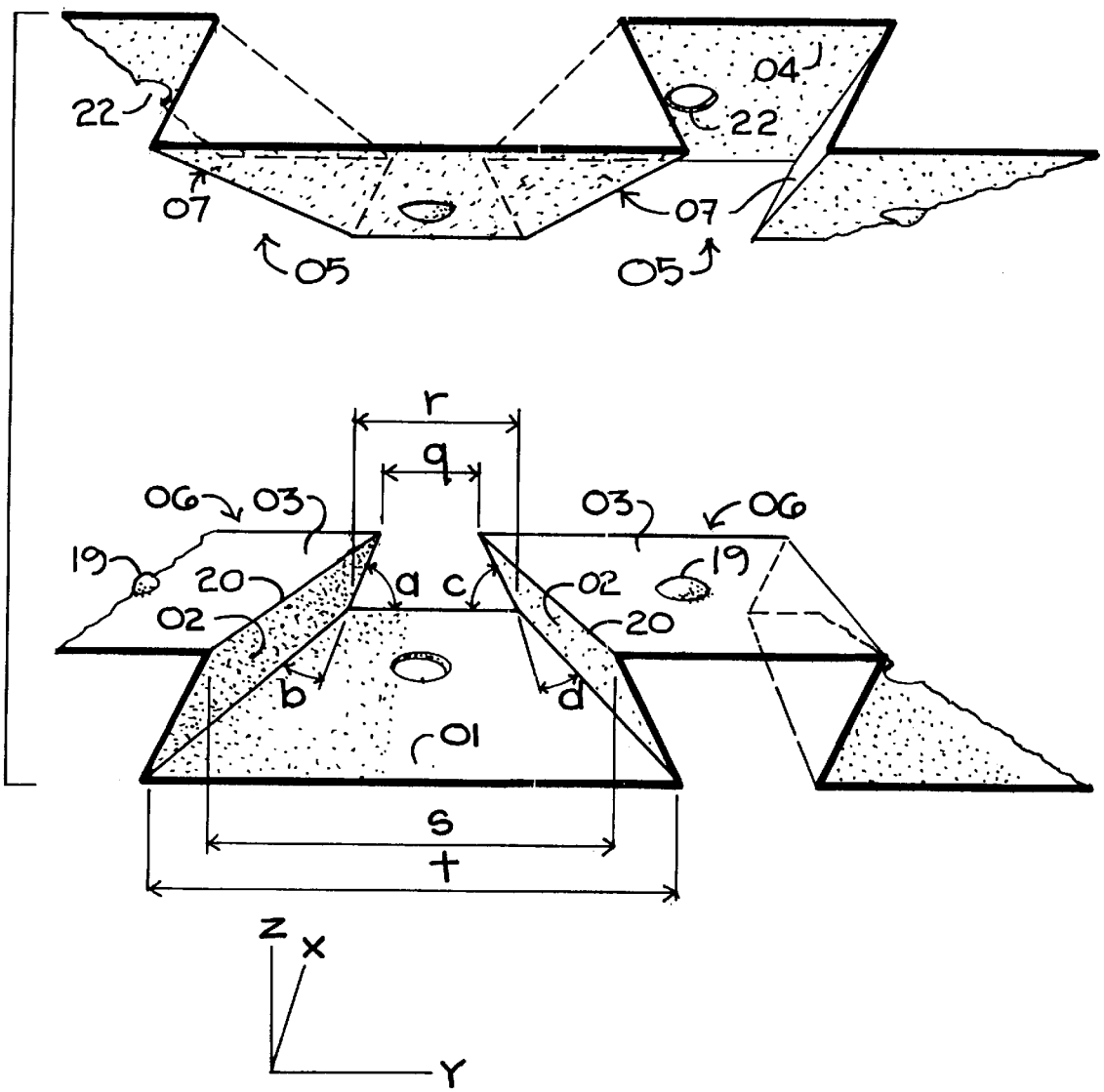
FIG. 1 is an exploded perspective view illustrating the essential mechanism and geometry of the interlocking device as well as one means of coupling the assembly.

Several preferred embodiments of the invention are herein schematically described all of which are variations of an interlocking device comprising: a first portion consisting of a first basal surface 01, and a first plurality of islands 06 provided thereon, each said island having a plurality of sidewalls 02 and a top surface 03; and a second portion having a structure projecting therefrom which provides a plurality of apertures 05 defined by a set of walls 07, one of which is a second basal surface 04. One or more of said islands 06 may thence be received in said apertures 05 by applying a relative shearing force so that sidewalls 02 are slidingly engaged by walls 07 as top surface 03 engages basal surface 04. Once so engaged, the device is resistant to further movement in direction x as well as to perpendicular forces in direction y or z or to rotational forces.

In general, individual islands 06 have a top surface 03 defined by a peripheral edge 20 and are configured so that the distance in a plane y-z measured between the sidewalls 02 of two adjacent islands is less between said peripheral edges than the distance as measured in the same plane at the basal surface. And further that when measured in a plane x-y, said sidewalls are not parallel and the y dimension between said sidewalls of two adjacent islands measured perpendicular to axis x is greater at one point than at another. Thus, in the embodiment illustrated in FIG. 1: dimension r is greater than q, dimension t is greater than s, dimension t is greater than r, the sum of angle a and angle c is less than 180 degrees, and the sum of angle b plus angle d is greater than zero and less than 180 degrees. Practicality generally limits these sums to an intermediate range.

As an island 06 on said first basal surface 01 may have a shape and size which are complementary to an aperture 05 on said second basal surface 04, and as the sidewalls 02 of two adjacent islands and the intervening basal surface 01 may define such an aperture, and vice versa, said first portion and said second portion may be considered as hermaphroditic in one or more aspects, although such hermaphrodicity is not essential to certain embodiments.

It is important to note at the outset of this description that this device may be shaped or configured in a wide variety of singular or plural embodiments, of orthogonal or rotundal aspect, and of whole or partial surficial elements, provided that each comprises the certain essential geometric aspects herein described.

For the purposes of this description the term "relative shearing force" shall mean a relative horizontal displacement of the basal surfaces in the x-y plane which may also include a simultaneous vertical component in a plane x-z as may draw the surfaces together as said shearing force is applied. "Lateral stress" shall mean a horizontal stress in the x-y plane. "Vertical stress" shall mean a stress in a direction z tending to separate said first and second basal surfaces. "Rotational stress" shall mean a combination of lateral or vertical stresses tending to rotate the engaged portions in opposite directions. "Hermaphroditic" shall mean the quality of both first and second portions having complementary male and female characteristics so that said portions are effectively interchangeable. "Structure" shall mean a singular or plural element of the device providing certain aspects and may include, but not be limited to, a plurality of islands. "Surface" shall mean all or part of a surficial element of the device which may include a basal surface, sidewalls, or walls. Axis x shall generally align with the predominant relative shearing force, parallel to said basal surface, which the device is intended to resist. Axes y and z are perpendicular to each other and to axis x.

It may be recognized that in the absence of a sufficient and consistent relative shearing force, the assembled device will generally remain engaged only because of inertia and friction on the contacting surfaces. The device may therefore be prone to inadvertent disconnection by a reversal of said relative shearing force. Friction may be enhanced in any embodiment by altering the texture or otherwise affecting the coefficient of friction on any contacting surface. Also, as one or more of the effective angles a, b, c, or d becomes more acute, inadvertent release by a lateral or vertical stress component is generally reduced in relationship to said angle. However, in this embodiment and others, diverse optional coupling means are additionally provided to maintain continuous engagement and therefore enhance the utility of the device.

In FIG. 1 one such coupling means is illustrated as a plurality of first coupling members 19, here shown as convex projections, provided on the top surfaces 03 of islands 06 which are designed to couple with a second set of coupling members 22, here shown as a plurality of apertures on basal surfaces 04 and 05 so that when the first and second portions are engaged said complementary coupling members are enjoined. In an hermaphroditic configuration said coupling members may be alternated on respective complementary surfaces. A lesser plurality may also be provided.

It is to be understood that this invention includes any type of coupling mechanism as may be employed to maintain engagement of the device. Such mechanisms may include, but are not limited to: a convex, polygonal. conical, curvilinear, or irregular shape projecting from any interengaging surface of either portion which couples with a complementary surface by causing a temporary distortion in said surface; any such aforementioned shape which couples with a complementary aperture or recess on the interengaging surface; any such aforementioned shape which effects a detent against any portion of the complementary member; a portion of a bolt, nail, rivet, staple, thread, wire, or other fastening device projecting from any interengaging surface of either portion so as to couple with and cause resilient distortion of the complementary surface; a portion of any such fastening device which couples with a complementary recess or aperture in the complementary surface; the head of any such fastening device which provides a detent against any portion of the complementary member; a surface which is temporarily distorted by engagement with another surface; a portion of a substrate material which provides a detent against the edge of an opposing island; a ridge, or plurality of same providing a serrated surface running generally perpendicular to or angular to the predominant shearing force engaging a like ridge or surface; a ridge running perpendicular or angular to the predominant shearing force so as to provide a detent against an edge of an engaged island; a three dimensional distortion of any surface meeting a complementary distortion of an engaging surface; a portion of a substrate material projecting through an aperture in an engaging surface; a magnet, latch or spring, any such aforementioned device which may be rigid or resilient in any portion. Certain, but not all, of these means will be seen illustrated in the subsequent embodiments of this invention and all may be considered as generally interchangeable between diverse embodiments and as applicable on any interengaging surface or edge of the device, in singular or plural number, without deviating from the overall scope of this invention.

Although the device is illustrated in FIG. 1 as having an orthogonal geometry, as having symmetrical components, and as having components arrayed linearly, considerable variation in form, proportion, plurality, continuity of surface, configuration or other aspect may be provided. Each embodiment herein illustrated is intended to schematically demonstrate particular aspects of the invention which may be otherwise combined or reconfigured in diverse variations.

Certain aspects of the basic embodiment illustrated in FIG. 1 are inherent in subsequent embodiments: Interlocking is accomplished by aligning complimentary sets of the device in opposed disposition and slightly offset from their final position, thence applying a relative shearing force until at least one island of the first portion engages at least one point on each of two walls and the basal surface of a complementary aperture. The device is generally self-aligning in that an initial relatively loose interspersal of the components is directed by the two-dimensional taper into a tighter and more precise alignment as the relative shearing force is applied. Stresses due to said relative shearing force tend to be resisted by both shear and tensile strain at the juncture of islands 06 with base 01. The force required for disassembly is unrelated to the strength of the connection in resistance to relative shearing forces. The interconnecting elements of the device, although having male and female characteristics in certain embodiments, are generally interchangeable in that the female aperture may be formed by the sidewalls of two adjacent male members and a basal surface, thereby effecting an optional hermaphroditic aspect. Coupling members of diverse form as discussed above may be incorporated in any embodiment of the device. The device in its many embodiments may be readily manufactured by common techniques using virtually any suitable material and it may be considerably varied in design within the parameters of the invention. When engaged, the device is effectively concealed from view. The advantages of these aspects and others will become apparent throughout this disclosure.

Elements of the device may be enjoined and configured in a two dimensional array so as to provide a connection that resists relative shearing forces in multiple directions. In the embodiment illustrated in FIGS. 2, 3, and 4, an hermaphroditic assembly having a plurality of islands 06 is provided on each basal surface 01. In this embodiment each island 06 is configured so as to provide a single actuating mechanism of the device facing each of four directions on plane x-y. Each island 06 has four undercut sidewalls 02 diagonal to the grid, the meeting corners of which are truncated, thus providing a top surface 03 defined by peripheral edge 20 having a polygonal perimeter in plan view. When so arrayed on a grid the islands thus formed each have an associated island width, diagonal dimension h of the top surface 03, which is slightly larger than the associated complementary aperture width, diagonal dimension k of the entrance opening provided between the peripheral edges of each of four adjacent islands.

The top surface 03 of each island 06 in this embodiment is conical in profile having a relatively small vertical dimension.

Said conical surface functions as an aid to alignment of the first and second portions. When two such surfaces are pressed toward one another, the top surface of opposing islands 03 may first contact at any point and then tend to slide laterally into alignment with corresponding aperture openings as with application of a relative shearing force. Once so aligned, the top surface 03 of each island is then forced into a corresponding aperture by causing a temporary deformation of corresponding peripheral edges 20 until the widest portion of the island is effectively trapped within the narrower portion of the aperture. Alternately, if said islands are provided of a rigid material and the basal surface is provided of a flexible material, said deformation may occur in the basal surface in lieu of the peripheral edges, As the surfaces are pressed further as in FIG. 3, the conical top surface 03 contacts the smaller conical protrusion 08 at the center of each space, which functions both as an angular guiding surface and as a first coupling member. Continuation of either a relative shearing force or a vertical force tends to direct island 06 laterally into a fully engaged position wherein sidewalls 02 are effectively engaged and coincident with the complementary walls of the corresponding aperture. Once so engaged, center protrusion 08 provides a detent against a portion of conical surface 03 here functioning as a second coupling member. Thus it can be seen that this embodiment effectively provides two stages of coupled engagement: the first being containment of the island by the overlapping peripheral edges; and the second being full engagement by application of a relative shearing force which slidingly engages the corespondent walls and basal surface with top surface.

Figure 2:
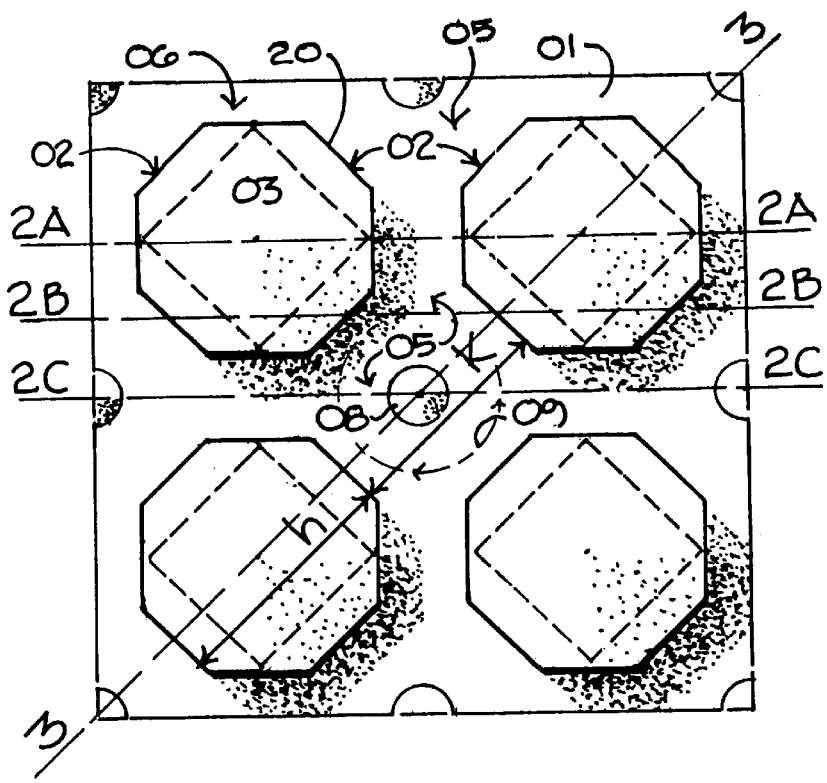
FIG. 2 is a plan view illustrating one portion of an embodiment of the interlocking device which connects surfaces subject to stresses in multiple directions as well as providing means of coupling the assembly in pre-engaged and engaged positions.
Figure 2A:
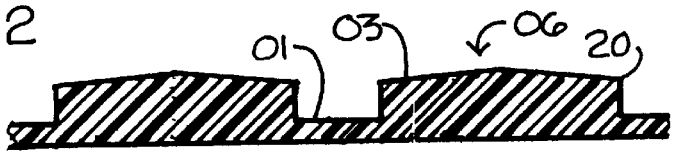
FIGS. 2A–C are sectional views of FIG. 2.
Figure 2B:
Figure 2C:
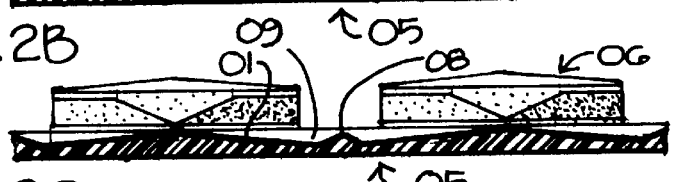
Figure 3:
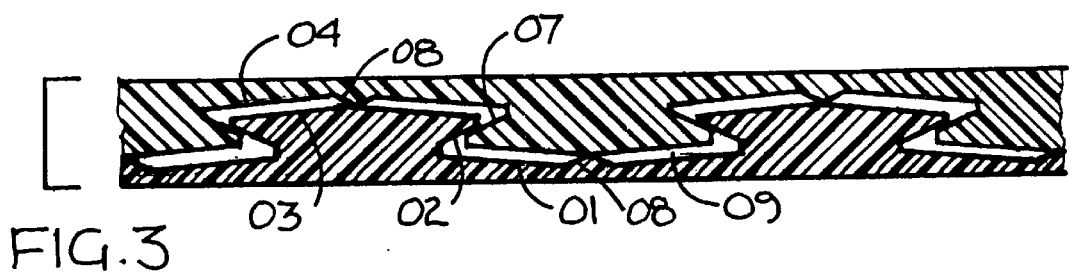
FIG. 3 is a sectional view of FIG. 2 illustrating the embodiment in a partially enjoined or pre-engaged position with a complementary second portion.
Figure 4:
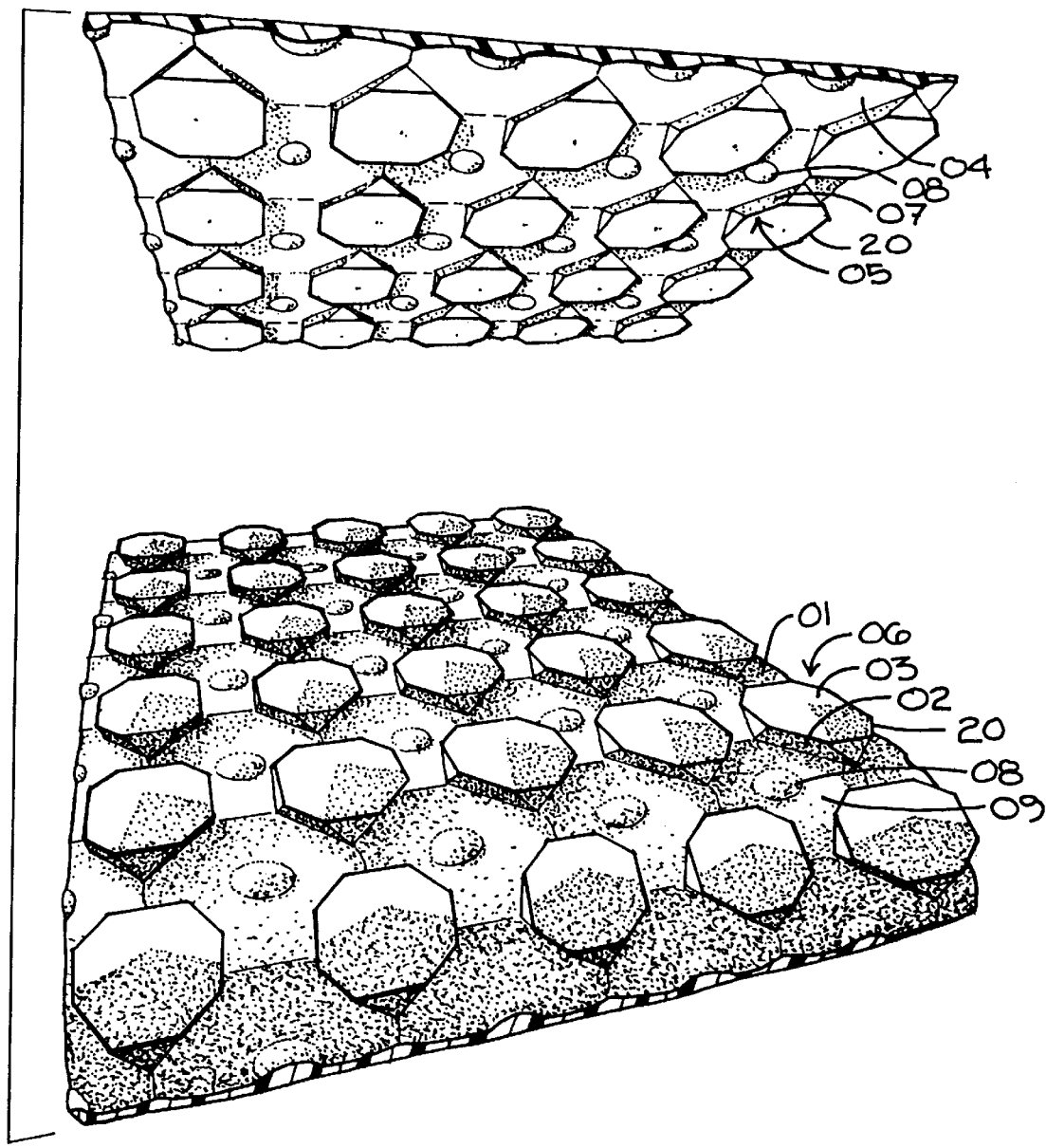
FIG. 4 is an exploded perspective view of the embodiment of FIGS. 2–3 on a flexible surface.

It may be seen that this embodiment FIGS. 2, 3 and 4 of the device is resistant to relative shearing stresses in any direction normal to the surface. When such stress is axial with the primary grid, engagement is effected in a manner similar to a plurality of the embodiment shown in FIG. 1. When such shearing force is diagonal to the grid, engagement is maintained by contact of opposed parallel sidewalls 02 effectively functioning as a pair of orthogonal wedges. When such stress is applied at any intermediate angle, a combination of these resistant means is provided. If, while the components are held in an engaged position, the direction of said shear force is shifted, each island may slide laterally within an effective channel 09 on base 01 that is defined by center protrusion 08 and the surrounding islands. Therefore an engagement is maintained which is resistant to inadvertent release and is adaptable to varying shear stresses.

Additionally, this embodiment may be resistant to vertical forces to a degree determined by design. As the vertical stress component is proportionally increased, engagement is first maintained by contact of the engaged sidewalls 02 until said vertical component overcomes the resistance provided by coupling members 08, 03 forcing an engaged island 06 to slide laterally to a centered position relative to the surrounding islands, whence said vertical force is resisted by the interengagement of opposed peripheral edges 20 as is the opposite force at initial insertion.

It is important to note that the vertical force required for release in this and other embodiments, which is essentially equal to the vertical force required for initial insertion, may be determined by design independently of the strength of the device in resistance to horizontal shear. Therefore, although primarily provided to resist stresses which are normal to the two interlocked surfaces, embodiments of this device may be designed to resist significant uplift stresses as well. First, it may be appreciated that a more acute vertical angle a, say forty five degrees or less, between an island sidewall and basal surface will provide greater resistant to vertical stress components than a design with a wider vertical angle because a relatively larger proportion of a sidewall 02 is acting against vertical stress. Secondly, the resistance to vertical forces at meeting peripheral edges may also be determined by design. Therefore, it may be seen that this invention may provide considerable advantage over extant devices employed primarily in a condition subject to relative shear.

When formed of and/or attached to a flexible base surface 01 as in FIG. 4, this embodiment can tolerate considerable three-dimensional flexing. As seen previously, the plurality of interengaged islands 06 each may move to a reasonable degree relative to one another by sliding horizontally without disengaging. When the plurality is engaged, individual islands 06 may slide within their respective channels 09 in order to accommodate flexure of the whole.

A variation of the previous embodiment is illustrated in FIG. 5. Herein a set of geometrically arrayed islands 06 are affixed to a semi-flexible base material such as a stiff fabric. Each island 06 is conically undercut so as to provide a continuously curved surface thus effectively providing an infinity of non-parallel sidewalls 02. Each island 06 is formed in profile such that at the peripheral edge 20 and corresponding innermost perimeter 21, adjacent to the conical section, a relatively short transition portion is provided as a means of avoiding sharp and/or brittle edges. A similar or curvilinear edge profile may be optionally provided in any embodiment as may be seen in subsequent drawings. The basal surface material 01 may be attached to a substrate material 10, which may be fabric, by sewing or otherwise fastening at the center point between each set of four islands. The resultant tuft of thread or, alternatively, fastener head 11 may be seen to approximate in function the central conical projection 08 of the previous embodiment, thus providing a first coupling member.

Connection is initiated by inserting each island into the somewhat smaller aperture width defined by the peripheral edges of four opposing islands, by the application of a vertical or relative shearing force. The top surface 03 of this embodiment is slightly convex in order to enhance alignment. Once so inserted, the device may then be fully engaged by application of a relative shearing force until the sidewalls 02 of each island, transition segments 20, 21, top surface 03 and basal surface 01 are each engaged with their counterpart. As a relative shearing force is applied, convex top surface 03 forces the semi-flexible basal surface 01 and substrate material 10 to deform slightly so as to accommodate said convex top surface 03, as seen in FIG. 5b. When fully engaged, the tuft of thread or fastener head 11, said first coupling member, maintains engagement by providing a detent against horizontal movement of top surface 03 functioning as the second coupling member.

This embodiment shares many of the characteristics of the preceding embodiment of FIGS. 2, 3 and 4 in that it is resistant to multi-directional stresses, may accommodate significant flexure, and may be designed so as to confine opposing islands in a first stage position independently from a second stage full engagement. It can be seen that in this embodiment FIG. 5 engagement of said opposing sidewalls effectively occurs along a single line where the said opposing sidewalls 02 contact rather than as a full surface interface of opposing sidewalls. However, the operating principle of a narrow aperture segment constraining a wider island segment applies. This embodiment also differs in that engagement is maintained by a combination of friction on surface 01, the resilient pressure caused by distortion of that surface 01, and by the horizontal resistance provided by effective coupling members 11 and 03.

FIG. 6 illustrates one embodiment of the invention which is configured so as to be primarily resistant to relative shear in two opposite directions. A plurality of oblong islands 06, of a curvilinear design approximating a hexagon in perimeter, are arrayed in a grid pattern on each hermaphroditic surface 01. Each island 06 has a curvilinear top surface 03 with undercut sidewalls 02 approximating a two dimensional diamond at its narrowest profile. All of the surfaces, including the sidewalls 02, are rounded in at least one dimension. A smaller pyramidal protrusion, centered axially between each island, provides a first coupling member 12.

As in other embodiments, interlocking is initiated by aligning the islands 06 of two portions parallel to an axis x so that application of a relative shearing force in either direction completes engagement. Once engaged, the diamond shaped first coupling members 12 on each side of an opposing island 06 confine the peripheral edge 20 of top surface 03 of said opposing island so as to maintain engagement of the two portions. When a relative shearing force is applied in the opposite direction, which is sufficient to overcome the resistance of coupling member 12, the island will slide into engagement in a reversed position in the aperture 05 provided between the next adjacent pair of islands and will be retained by the opposite sides of first coupling members 12.

As in the two previous embodiments, a first stage of engagement may be optionally provided by sizing the associated island width of top surface 03 of a first plurality of islands, as defined by peripheral edge 20, slightly larger than the complementary associated aperture width provided between adjacent islands, thereby requiring a slight distortion of said edges or basal surface 01 in order to initiate engagement. It should be noted that the longitudinal proportion of this type of embodiment, in comparison to other embodiments, tends to proportionally increase the engaged surface area of opposed sidewalls 02 subject to a relative shearing force aligned with axis x. However, the functioning surface area resistant to shearing forces in direction y is proportionally smaller.

Figures 7, 7A, 7B:
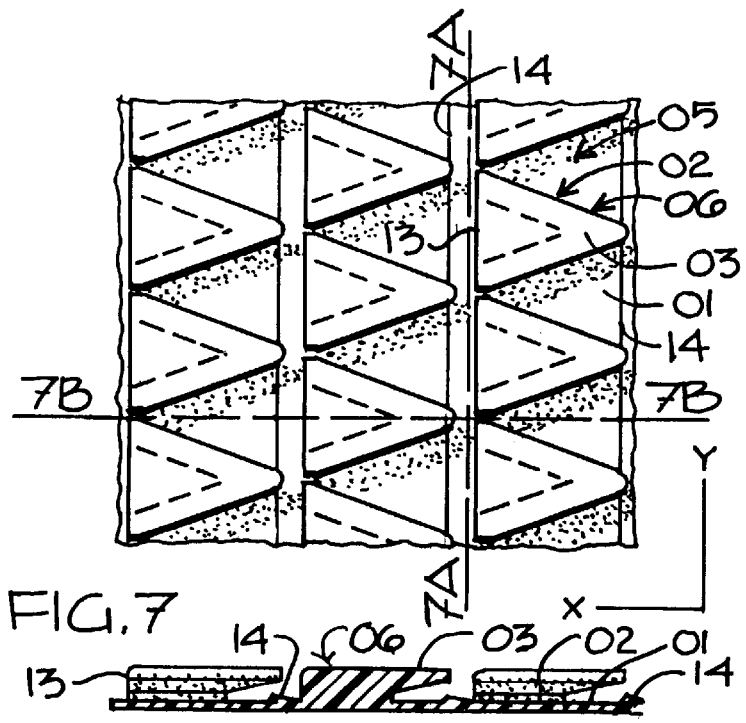
FIG. 7 is a plan view of a portion of an embodiment designed to connect two surfaces subject to shear stresses primarily from a single direction, as well as another coupling means.
FIGS. 7A–B are sectional views of the embodiment of FIG. 7.
Figures 8, 8A, 8B:
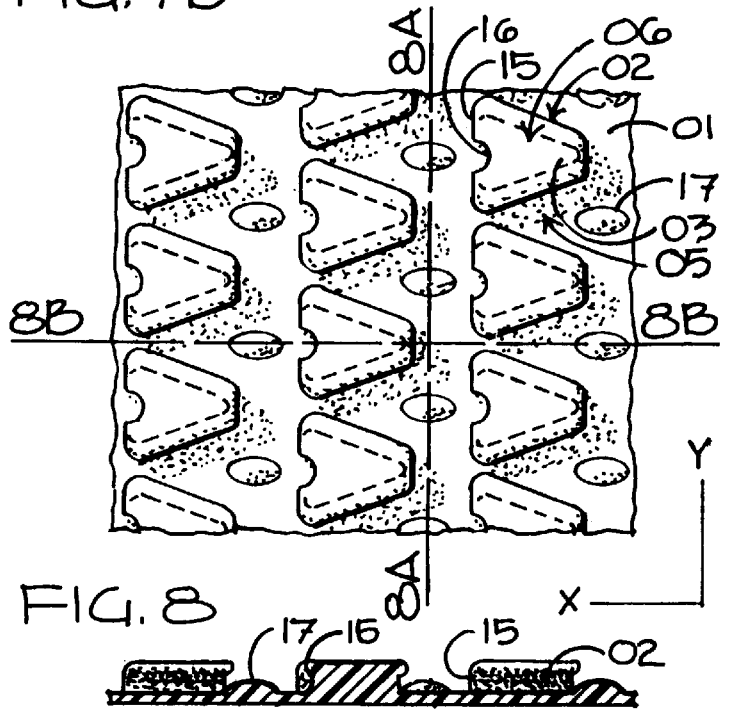
FIG. 8 is a plan view of a portion of another embodiment designed to connect two surfaces primarily subject to one directional stress, as well as yet another coupling means.
FIGS. 8A–B are sectional views of the embodiment of FIG. 8.

FIG. 7 and FIG. 8 both illustrate pluralities of the islands 06 arrayed on a surface which are configured so as to primarily resist a relative shearing force in a single direction. Both consist of geometrically arrayed pluralities of said islands having top surfaces 03 with perimeters approximating a triangular shape in plan view, two sidewalls of which 02 are undercut to provide an acute angle with surface 01.

In FIG. 7 the islands 06 and intervening apertures 05 are essentially orthogonal with peripheral edges 20 relieved. A continuous longitudinal ridge 14, contiguous with basal surface 01, intersperses each row of islands in direction y so as to provide a first coupling member, and each islands has a third side 13 the peripheral edge of which provides a second coupling member. Connection is initiated by interdigitating sets of islands in opposite disposition and applying a relative shearing force so that each island 06 of one array fills the aperture 05 formed by its opposites. When the projection becomes fully engaged, said engagement is maintained by the latch affected by coupling member 14 engaging coupling member 13, the third edge of said island. Thus a connection is achieved which is primarily resistant to relative shear in one direction and may also resist disconnection to a degree determined by the design of said coupling members. Additionally, as in other embodiments, the associated island and aperture widths may be dimensioned by design so as to provide a first stage coupling independently resistant to vertical stress.

In the embodiment illustrated in FIG. 8 the islands 06 are more curvilinear in design and the third side 15 of each island provides a concave indentation 16 on its peripheral edge as a coupling member which, when the device is engaged, coincides with a convex protrusion 17 on the surface 01 which provides a second coupling member. Connection is initiated by application of a relative shearing force so that triangular islands 06 occupy apertures 05. When an island 06 is in its engaged position, the coupling member 17 also engages its mating receptor member 16.

As in other embodiments, these versions of the device FIGS. 7 and 8 may also have ready application for use in connecting flexible materials. When basal surface 01 allows reasonable flexure in one or more directions, flexibility of the device is limited in direction y by the space between the peripheral edges of adjacent islands and only by the flexure likely to cause disassembly in direction x.

Figure 9:
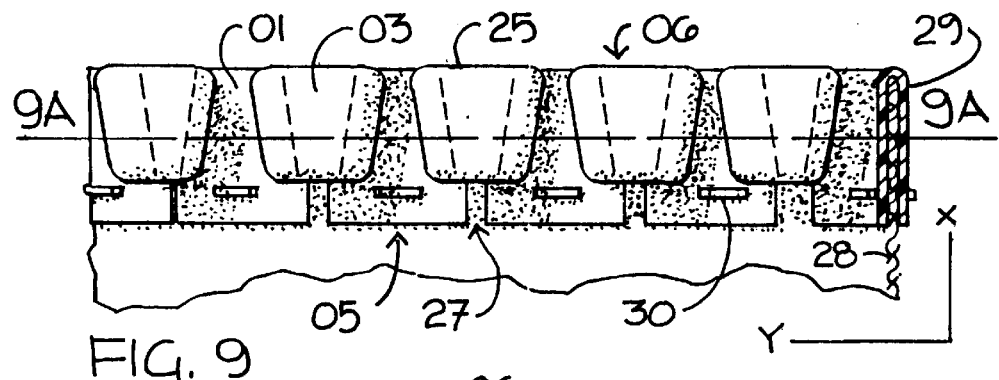
FIG. 9 illustrates one portion of an embodiment in plan view of the interlocking device in which a plurality of islands are arrayed along the edge of a flexible material, as well as a coupling means which also attaches the device to a substrate.
Figure 9A:
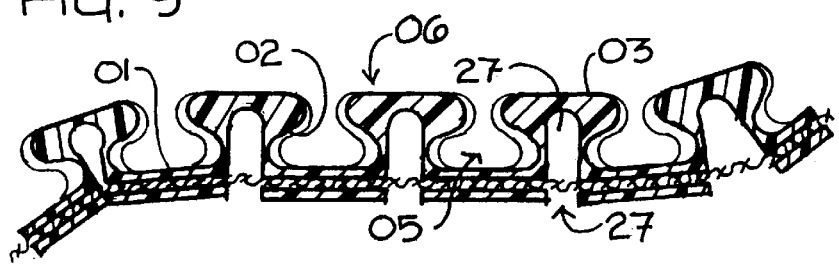
FIG. 9A is a sectional view of the embodiment of FIG. 9.

FIG. 9 illustrates an embodiment in which a plurality of curvilinear islands with rhomboidal perimeters 06 are arrayed in parallel along a connecting edge. Each adjacent pair of islands is affixed to a common basal surface 01 which is separated from its neighbor by a division 27 extending upward into the body of said island. Therefore, when manufactured of a reasonably resilient material, a continuous, partially segmented, connector strip is provided which can flex to a reasonable degree along axis y, said degree predetermined by the dimension of division 27. Each common segmental link of basal surface 01 is provided so as to fold 180 degrees over a substrate material such as fabric 28 so that the back side 29 may align with the upper side 01. The assembly is then attached to the substrate by a fastener 30, which may be a staple, rivet, sewn thread, or other common device protruding through each link, allowing a small degree of slack in the substrate at 27 so that the whole may flex. When aligned with a second portion of similar design in and a relative shearing force is applied, the assembled device may be held in place by the latching effect afforded by the protruding staple or thread 30, which here serves as a first coupling member, providing a detent against the rear peripheral edge 25 of top surface 03. Thereby, a continuous, reasonably flexible lineal connection is provided which may be utilized, for example, in many applications where press-together or zipper type fasteners might otherwise be employed.

Figure 10:
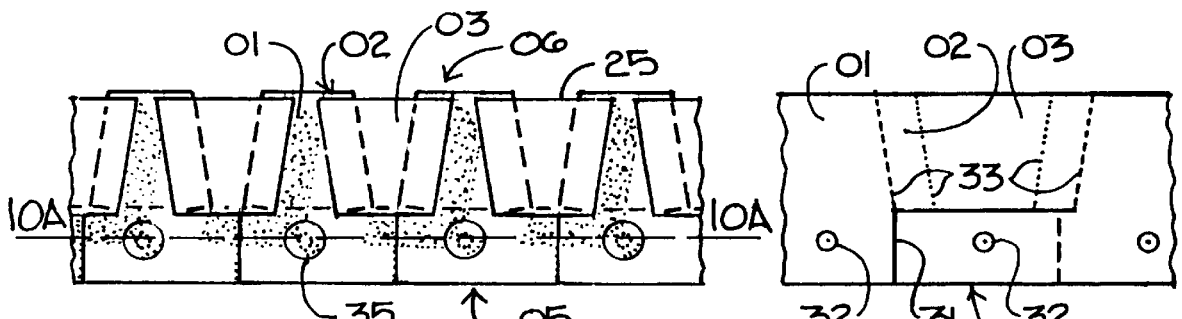
FIG. 10 is a plan view of one portion of an embodiment of the device fabricated of a formed sheet material, as well as a coupling means that also attaches the device to a substrate.
Figure 11:
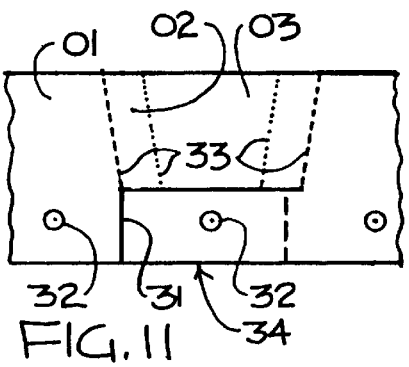
FIG. 11 is a plan view of the embodiment of FIG. 10 as a flat sheet prior to forming.
Figure 10A:
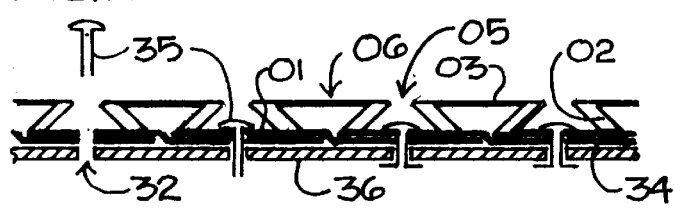
FIG. 10A is a sectional view of the embodiment of FIG. 10 in a partially assembled condition.

FIGS. 10 and 11 illustrate an embodiment of the device as it might be manufactured of a single piece of malleable thin material such as sheet metal. FIG. 11 indicates a portion of such a continuous flat sheet which is to be formed by cutting at an edge 31, creating a secondary aperture at 32, then folding at 33 and extending tab 34 until adjacent secondary apertures 32 align. The formed device as shown in FIG. 10 may then be fully assembled by inserting a rivet or similar device 35 through the aligned secondary apertures 32 as well as into a substrate material 36. Said substrate material may be wholly below the surface or sandwiched between alternate layers of the base material. The head of said rivet or similar device 35 may provide a first coupling member which will provide a detent against the rear peripheral edge 25 of an island in engaged position. Therefore a lineal connector is provided of a sheet material in which the individual islands 06 are hollow.

An alternative coupling mechanism in this and other embodiments, which may be used optionally along with the diverse means provided, is to design the correspondent islands and apertures of each portion so that each island is somewhat larger than each aperture, thereby causing a temporary resilient distortion in one or more of the engaging surfaces, such distortion providing substantial pressure on such engaged surfaces so as to effectively lock the portions in engagement.

FIGS. 12 and 13 illustrate two embodiments which specifically provide for linear adjustability, each having a first portion having a plurality of islands arrayed along the primary axis x so that interconnection can occur by engaging the islands with the apertures of a second portion at any point along the axis. Although illustrated here as having a singular row in width, it can be readily understood that any plural embodiment of the device can likewise provide adjustability. Multiple rows may be employed in order to provide greater strength and/or stability where required or to provide lateral adjustability as well.

The embodiment shown in FIG. 12 consists of a rigid or flexible first portion 41 having a plurality of apertures 05 in a linear array, each defined by first and second sidewalls 40, 43 extending transversely to coordinates x-y-z and a chevron shaped basal surface 04 having a truncated chevron perimeter. A plurality of islands 06 is linearly arrayed on a second portion 42, as might be the opposite end of a contiguous belt, each island having transversely sloped sidewalls 02,39 a top surface 03 with truncated chevron perimeter and inversely sloped rear walls 39. The islands of the second portion being located so as to define a second aperture 38 between each adjacent pair, said second apertures being similar but of an inverse configuration to those of the first portion. Likewise, a similar but oppositely configured plurality of islands 37 are inversely configured on the first portion so that when juxtaposed with one or more of the islands of the second portion said islands fill said apertures, thus effecting a segmented whole.

Adjustability is afforded by bypassing the opposed straps, or ends, to a point slightly beyond a desired register or tension, thence initiating engagement by applying a relative shearing force to islands 06 and 37, thereby slidingly engaging the sidewalls and top surface of each island against the complementary aperture walls of its counterpart. It may be appreciated that this embodiment offers a considerable advantage over ratchet-like or serrated coupling devices in that the two portions of the device are effectively self aligned by the three-dimensional diagonal geometry of the chevron shaped islands. It may also be appreciated that such an embodiment may be provided so as to have a linear plurality of islands on one portion which adjustingly intersperse with a singular or lesser plurality of islands on a second portion, thus providing an adjustable connection between an axial member and a point.

FIG. 13 illustrates an embodiment which provides for adjustability and shearing force resistance in two opposite directions along axis x. A plurality of diamond shaped islands 06 in linear array, affixed to a first basal surface 01, on first portion 46 are transversely undercut in two directions forming sidewalls 02. A structure is provided on a second portion 47 having a linear array of apertures 05 defined by the undercut walls 07 and second basal surface 04. The structure is illustrated as having an optional division 44 forming separate links in order to allow for lineal flexibility. When aligned and engaged by application of a relative shearing force at any desired point of adjustment, the device provides resistance to stresses acting in either direction along axis x. By providing islands of a somewhat larger associated island width than the corresponding associated aperture width, this embodiment may also be designed to independently resist vertical stress as in previous embodiments.

FIG. 14 illustrates an embodiment of the device which provides a continuous lineal seal as might be utilized to close a plastic food storage bag or similar pouch type container commonly provided of flexible material. A plurality of islands 06 are provided on a first portion in a linear array parallel to an axis y. Each such island has sidewalls 02 which are laterally contiguous with a connecting link 50 between each two adjacent islands so as to provide a continuity of such connected sidewalls, which further may be optionally connected with the second portion at one or both ends of such continuity. Each island in the continuity has a top surface 03 which is also continuous between adjacent islands. A similarly shaped structure is provided on the second portion having a continuity of complementary apertures each formed as the inverse of adjacent islands. Each island top surface 03 has a rear edge, portions of which provide a first coupling member 48 which, when an island and complementary aperture are engaged, couples with a second coupling member 49 protruding from the basal surface between each opposed island pair. Such coupling members are designed and configured so as to provide, when coupled, continuous pressure on said islands, thus forcing a sealed condition at the continuously engaged interface by compressing the complementary surfaces. When manufactured of a flexible sheet material providing the desired profile, the device may be readily connected by squeezing the opposing portions into engagement and easily released by pulling the two portions apart. The visual appearance of protrusions 49 when engaged with the opposed surface 01 may be designed to provide readily visible evidence of closure, as does the tactile feel of the engaging links when actuating closure by squeezing the assembly from one end to the other.

Embodiments of the device may be provided in which a portion of any surface, or an appendage on any surface, may be of electrically conductive material and another portion of electrically insulative material, separating electrical circuits, so as to provide an electrical interconnecting device when the portions are engaged. For example, a portion of the top surface of an island may conduct an electrical current to a portion of the complementary basal surface. In general, in order to protect unconnected conducting surfaces from inadvertent contact, it is desirable to provide such contact surfaces on the undercut sidewalls of adjoining islands, providing other surfaces of the device as electrically insulative.

One embodiment of the device which provides an electrical connector for one or more circuits is illustrated in FIGS. 15 and 16, here shown as half of an hermaphroditic connector. One or more islands 06 is provided of an insulating material having receptacles internal to each island 66 defined by first, second, and third walls. The transverse sidewalls 02 of each island are provided with a first slot 53 coincident with said sidewalls and internal walls. A tapered plug 51. Of insulative material, is configured so as to fit snugly within said receptacles, having four walls and slots 56 on its sloped sides which are sized to receive an electrical conductor. The third wall of the receptacle is provided with a first coupling member 52 which engages a second coupling member 55 on the fourth wall of plug 51. A conductor 54 is inserted so as to align with slots 53 and 56, as plug 51 is inserted into its receptacle until firmly held by coupling members 52 and 55 thereby causing conductor 54 to fill slot 53.

When the assembly thus formed is then enjoined with a like assembly in opposite disposition and a relative shearing force is applied, a connection is effected which forces each conductor 54 into contact with its counterpart. The interconnected whole may be held in engagement by coupling members similar to 52 and 56, which are here illustrated as complementary serrated surfaces. Other means of coupling such as those shown herein in association with other embodiments may be substituted. Proper alignment of multiple conductors may be predetermined by altering the size of one or more of island and apertures in a set so that only one alignment is possible or by providing an otherwise asymmetrical design.

It is to be understood that this embodiment represents only one of many possibilities for providing an electrical connection utilizing the basic mechanisms of this invention. Some distinct advantages of utilizing this invention as an electrical connector include the following: Conducting surfaces may be protected from exposure. A strong tensile connection is readily achieved. No pins or other delicate exposed parts are subject to damage. A large plurality of conductors can be accommodated in a relatively small cross sectional area. And, modular components may be rigidly connected physically and electrically without external wires.

A singular interlocking device is illustrated in FIGS. 17 and 18 which also demonstrates two additional coupling means to maintain engagement. Also illustrated is how a plurality of individual islands and apertures may be enjoined 57, 62 to provide a continuous lineal connector. An embodiment is shown having a complementary aperture FIG. 17, and island FIG. 18, either of which may be configured with a like member 57, 62 so as to provide an effective projection of the opposite gender.

FIG. 17 illustrates a method of locking the device in an engaged condition by provision of a first locking member 58 which here is a moveable portion of the base surface 01 severed along line 59 and resiliently hinged at 60. As a complementary island as in FIG. 18 is engaged in the aperture, locking member 58 is deformed until top surface 03 is fully engaged in contact with basal surface 04. Thence raised edge 59 engages the rear edge 25 of surface 03 as a latch, thus maintaining the assembly until locking member 58 is again depressed to the level of surface 01. FIG. 17 also illustrates a connection to a substrate fabric similar to that shown in FIG. 9.

FIG. 18 illustrates a relatively simple means of coupling the device in conjunction with a means of attaching the device to a substrate material, as might be used in an application connecting fabric components. Here a substrate fabric edge 61 is attached so that it aligns with the back of island 06, by sewing or otherwise attaching the connector to the fabric. In this way attachment of the device and hemming of the joining edge may be accomplished in a single operation. When thence engaged with an island such as shown in FIG. 17, the substrate edge, which is temporally compressed during insertion, expands along edge 61 so as to latch the assembled connector in its engaged position.

FIG. 19 illustrates yet another embodiment of the present invention which is a singular interlocking set comprising three parts which may be attached to a fabric or other flexible substrate material while forming a pleat in said material. A first portion being a tapered plug 63, having a first locking member 67 on one side, is wrapped within a fabric or other flexible substrate 69 and inserted into a receptacle 64 so that locking member 67 forces a portion of the substrate to deform and project through a slot 68 in a wall of the second portion. The substrate 69 is thereby firmly attached by the connection created at 67, 68 which also causes a pleat to extend axially parallel to axis x. This assembly may then be slidingly engaged in a third portion 65 providing a complementary aperture. The protruding substrate material provides a third coupling device by causing contact of substrate 69, projecting through slot 68, with the basal surface 04 of 65 causing temporary distortion therein. The assembled embodiment is illustrated in FIGS. 20, 20A.

The interlocking device as illustrated in this embodiment FIG. 19 therefore provides a means of directly attaching a fabric to the connector without requiring sewing or other attachment means. Singular or plural configurations of such an embodiment of the device may have considerable utility.

Figure 21:
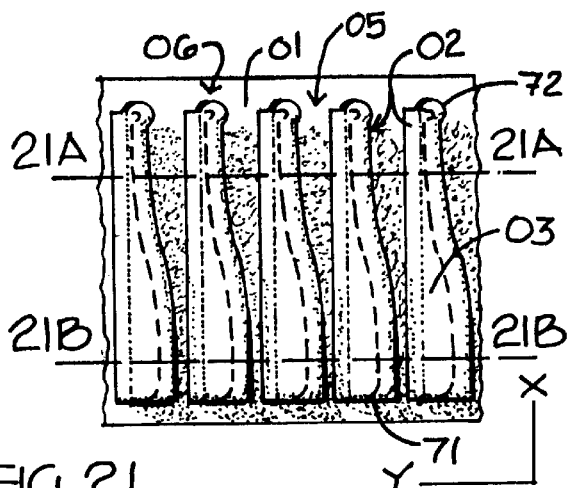
FIG. 21 is a plan view showing one portion of an embodiment with an asymmetrical aspect in both plan view and profile and in which one of the sidewalls of each island is configured at an obtuse angle to the basal surface, as well as yet another means of coupling the assembly.
Figure 21A:
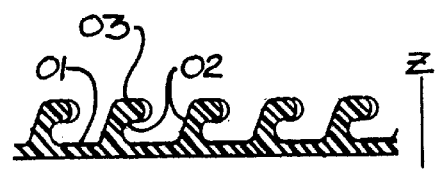
FIGS. 21A–B are sectional views of the embodiment of FIG. 21.
Figure 21B:

FIG. 21 illustrates an embodiment which is asymmetrical in both its plan and profile. In this case the sidewalls 02 of each island are of differing aspect: one being a planar surface set at an oblique angle to basal surface 01, and running generally parallel to axis x; the other being a three-dimensionally curved surface generally transverse to axis x, y and z. The overall unit shape, however, effects the general two-directional convergence that is seen in other embodiments of the device, and provides an interlocking configuration when engaged with a similar plurality, of opposite hand, in opposed disposition. Such an asymmetrical aspect may be useful in connecting two objects subject to particular tangential or rotational loading characteristics. It may also effect a means of maintaining engagement in applications where the predominant shearing load is tangential to axis x. Additionally, asymmetry may be incorporated into any embodiment in order to prevent an inadvertent, non-desired connection between surfaces, so as to effect a male and female aspect rather than hermaphroditic.

FIG. 21 also illustrates another type of integral latching mechanism for coupling the engaged portions. In this embodiment a resilient or deformable bulb-like protrusion 72 provides a first coupling member extending from a portion of the peripheral edge of top surface 03 at the narrow end of island 06. When the portions are fully engaged, this protrusion expands into a complimentary space 71 provided by the curved end of sidewall 02 so as to latch against said sidewall edge.

Figure 22:
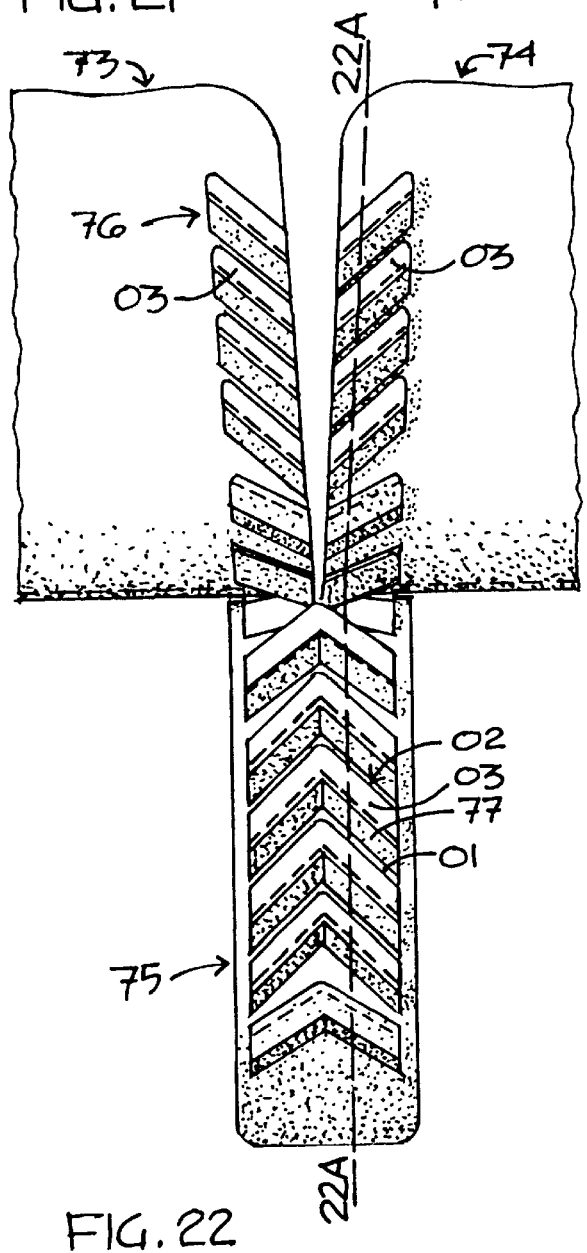
FIG. 22 is a plan view illustrating an embodiment of the device that interlocks two adjacent coplanar members with a third.
Figure 22A:
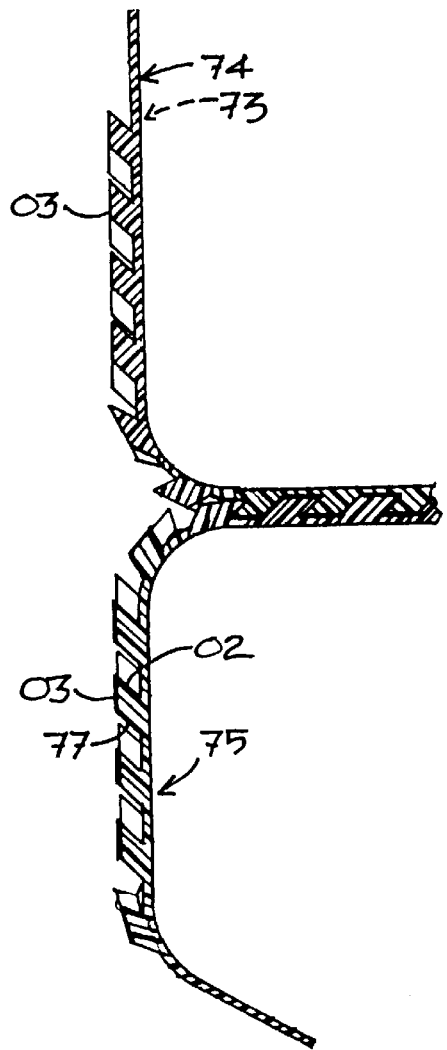
FIG. 22A is a sectional view of the embodiment of FIG. 22.

An embodiment is illustrated in FIG. 22 which provides a means of connecting the edges of two coplanar portions 73, 74 by attaching each to a first portion 75. Such an embodiment might be visualized as the two sides and tongue of a shoe. The first portion 75 is configured as a lineal plurality of apertures, each having a perimiter edge which is chevron shaped in plan view and having first 02 and second sidewalls 77 which are transverse to coordinates x-y-z. Sidewall 02 of this first portion forms an acute angle with the basal surface, sidewall 77 forming a complementary oblique angle. The second and third portions with coplanar edges, having mutual x, y and z coordinates, each providing a plurality of islands 76, each island having third and fourth, or fifth and sixth, sidewalls running generally parallel to one another and transverse to the x-y-z coordinates in complement to 02 and 77. Each island of the second and third portions comprises one half of an island pair, thereby jointly forming a bisected chevron-shaped top surface 03 in plan view. By applying a relative shearing force, or by sequentially rotating, the islands of the first portion 75 are slidingly engaged with the enjoined half islands on each edge of 73, 74 thereby drawing these portions into alignment, as sidewalls 02 and 77 of each link engage with the third, fourth, fifth, and sixth sidewalls of each island pair. When fully connected, the surfaces of portions 73 and 74 are aligned in a coplanar whole which may subsequently be released by reversing the process. Coupling means may be provided such as in other embodiments, by providing resilient islands which are slightly larger in at least one dimension than their respective apertures, or by coupling only the ends of the enjoined lineal pluralities thereby precluding disassembly of the intervening members.

It is to be understood that the above description and associated drawings are intended to schematically demonstrate a wide range of embodiments which utilize the effective mechanisms and geometry of this invention. Although it is not possible to herein describe all possible combinations and configurations it is the intent of these documents to demonstrate by examples a complete range of this invention which may utilize said effective mechanism and geometry in diverse combinations. It is further intended that all matters contained in the foregoing description or shown in the accompanying drawings shall be interpreted as schematically illustrative and not in a limiting sense.

The following claims are intended to cover the generic and specific features of the invention herein described, and all statements of the scope of the invention which, as a matter of language, might be said to fall therebetween.

I claim the following:

1. An interlocking device comprising:
   a. a first portion including a first basal surface and a first plurality of islands provided thereon, each of said islands having a plurality of sidewalls,
   b. a second portion including a structure having a plurality of apertures formed therein and a plurality of walls defining said plurality of apertures,
   c. said first plurality of islands being positioned on said first basal surface and configured so that said first plurality of islands may be received in said plurality of apertures; and
   d. said plurality of sidewalls and said plurality of walls being configured so that when said first plurality of islands is positioned in said plurality of apertures, application of a relative shearing force to said first and second portions causes ones of said plurality of sidewalls to slidingly engage corresponding respective ones of said plurality of walls until said ones of said plurality of sidewalls engage said correspondingly respective ones of said plurality of walls sufficiently to block further relative movement in a direction of said relative shearing force with the result that a greater force is required to remove said first plurality of islands from said plurality of apertures along an axis extending perpendicular to said first basal surface after application of said shearing force than before.

2. An interlocking device as in claim 1, wherein each of said first plurality of islands has a top surface with a peripheral edge, and said plurality of sidewalls are configured so that the distance between adjacent islands is less at said peripheral edges than at said basal surface.

3. An interlocking device according to claim 1, wherein said first portion has mutually orthogonal X, Y and Z coordinates, further wherein at least one of said plurality of sidewalls extends transversely to said X, Y, and Z coordinates.

4. An interlocking device according to claim 3, wherein said at least one of said plurality of sidewalls forms an acute angle with said first basal surface.

5. An interlocking device according to claim 3, wherein said at least one of said plurality of sidewalls forms an obtuse angle with said first basal surface.

6. An interlocking device according to claim 3, wherein said plurality of walls are configured so that said corresponding respective ones of said plurality of walls extend substantially parallel to said ones of said plurality of sidewalls when said first plurality of islands is received in said plurality of apertures.

7. An interlocking device according to claim 1, wherein said first plurality of islands is arranged as a linear array.

8. An interlocking device according to claim 1, wherein said first plurality of islands is arranged as a two-dimensional array.

9. An interlocking device according to claim 1, wherein said structure includes a second plurality of islands.

10. An interlocking device according to claim 9, wherein said first plurality of islands and said second plurality of islands are hermaphroditic.

11. An interlocking device according to claim 1, wherein said structure includes a plurality of first coupling members in communication with ones of said plurality of apertures, further wherein said first portion includes a plurality of second coupling members provided on ones of said first plurality of islands, said plurality of first coupling members being designed to couple with said plurality of second coupling members.

12. An interlocking device according to claim 11, wherein said first and second coupling members are positioned and configured so that when said first plurality of islands is positioned in said second plurality of apertures, said first and second coupling members couple following application of said shearing force so as to maintain said first portion in registration with said second portion.

13. An interlocking device according to claim 11, wherein said plurality of first coupling members is provided on said walls defining said plurality of apertures and said plurality of second coupling members is provided on said sidewalls of said first plurality of islands.

14. An interlocking device according to claim 11, wherein each of said plurality of apertures has a base and each of said first plurality of islands has a top surface, said plurality of first coupling members being positioned on said bases of said plurality of apertures and said plurality of second coupling members being positioned on said top surfaces of said first plurality of islands.

15. An interlocking device according to claim 11, wherein at least one of said plurality of first coupling members projects into a corresponding respective one of said plurality of apertures.

16. An interlocking device according to claim 11, wherein at least one of said plurality of first coupling members has a recess that communicates with a corresponding respective one of said plurality of apertures.

17. An interlocking device according to claim 11, wherein each of said first plurality of islands has a top surface, further wherein at least one of said plurality of second coupling members projects above said top surface of a corresponding respective one of said first plurality of islands.

18. An interlocking device according to claim 11, wherein each of said first plurality of islands has a top surface, further wherein at least one of said plurality of second coupling members has a recess that extends beneath said top surface.

19. An interlocking device according to claim 11, wherein each of said first plurality of islands have an edge, further wherein said plurality of second coupling members include said edge.

20. An interlocking device according to claim 1, wherein said first basal surface is more flexible than at least one of said plurality of islands.

21. An interlocking device according to claim 1, wherein each of said first plurality of islands has a top surface with a peripheral edge, further wherein portions of at least one of said first plurality of islands adjacent said peripheral edge are more flexible than other portions of said at least one of said first plurality of islands.

22. An interlocking device according to claim 1, wherein each of said plurality of apertures has an associated aperture width and each of said first plurality of islands has an associated island width, further wherein said aperture width for a given one of said plurality of apertures is less than said island width for a one of said first plurality of islands designed for receipt in said given one.

23. An interlocking device according to claim 1, wherein at least one of said first plurality of islands has a top surface with a circular configuration.

24. An interlocking device according to claim 1, wherein at least one of said first plurality of islands has a top surface with a polygonal configuration.

25. An interlocking device according to claim 1, wherein at least one of said first plurality of islands has a top surface with a non-circular, non-polygonal configuration.

26. An interlocking device according to claim 1, wherein said first portion has at least one surface that is electrically conductive and at least one surface that is electrically insulative.

27. An interlocking device according to claim 1, wherein said second portion has at least one surface that is electrically conductive and at least one surface that is electrically insulative.

28. An interlocking device according to claim 1, wherein said first basal surface and said first plurality of islands are formed from a single piece of material.

29. An interlocking device according to claim 1, wherein said second basal surface and said structure are formed from a single piece of material.

30. An interlocking device according to claim 1, further comprising:
   a. wherein said first portion has mutually orthogonal X, Y, and Z axes;
   b. wherein each of said first plurality of islands is positioned and configured to be received in a complementary one of said plurality of apertures so ones of said plurality of sidewalls engage complementary ones of said plurality of walls, said ones of said sidewalls extending transversely to said X, Y, and Z axes; and p1 c. further wherein ones of said first plurality of islands are larger, as measured in at least one dimension, than said complementary ones of said plurality of apertures in which said ones are received, and at least one of said first and second portions has flexible sections that temporarily deform when said ones of said first plurality of islands are moved into and removed from said complementary ones of said plurality of apertures.

31. An interlocking device according to claim 30, wherein said second portion includes a second plurality of islands, further wherein adjacent islands in said second plurality of islands are separated from one another by one or more of said plurality of apertures.

32. An interlocking device according to claim 30, wherein said first plurality of islands is arranged as a linear array.

33. An interlocking device according to claim 30, wherein said first plurality of islands is arranged as a two-dimensional array.

34. An interlocking device according to claim 30, wherein said structure includes a second plurality of islands.

35. An interlocking device according to claim 30, wherein said first plurality of islands and said second plurality of islands are hermaphroditic.

36. An interlocking device according to claim 30, wherein said first and second portions each have at least one surface that is electrically conductive and at least one surface that is electrically insulative.

37. An interlocking device according to claim 1, wherein ones of said first plurality of islands have a top surface, further wherein said top surface is configured so as to direct ones of said islands into approximate alignment with ones of said apertures when subjected to a relative compressive force acting in a direction generally perpendicular to said basal surface.

38. An interlocking device according to claim 37, wherein said first portion includes a plurality of first coupling members positioned on said basal surface, further wherein said top surfaces and said plurality of first coupling members are designed so that continuation of said relative compressive force after said top surface meets one of said plurality of first coupling members causes said ones of said islands to move laterally so as to effect said relative shearing motion.

39. An interlocking device according to claim 1, wherein said plurality of apertures and said first plurality of islands are arranged in a two dimensional array, said first plurality of islands and said plurality of apertures being configured so as to allow said relative sliding engagement as a result of application of said relative shearing force in a first direction normal to said basal surface, and said first plurality of islands and said plurality of apertures being configured so as to allow said sliding engagement as a result of application of a different relative shearing force in a second direction normal to said basal surface.

40. An interlocking device according to claim 39, wherein said first plurality of islands and said plurality of apertures are configured so as to allow said first portion to maintain engagement with said second portion when said relative shearing force in said first direction is shifted to said different relative shearing force in said second direction such that said greater force is required to remove said first plurality of islands from said plurality of apertures after application of said different relative shearing force.

41. An interlocking device comprising:
a. a first portion including a first plurality of islands;

b. a second portion including a structure having a plurality of apertures formed therein, wherein ones of said plurality of apertures are positioned and configured to receive complementary ones of said first plurality of islands, wherein said ones of said plurality of apertures have entrance openings that are smaller than said complementary ones of said first plurality of islands; p1 c. engagement means for permitting sections of said structure adjacent said ones of said plurality of apertures to slidingly engage said complementary ones of said first plurality of islands following application of a shearing force extending in a first direction to at least one of said first and second portions until said sections of said structure engage said complementary ones of said first plurality of islands sufficiently to block further relative movement in the direction of said relative shearing force with the result that a greater force is required to remove said complementary ones of said first plurality of islands from said ones of said plurality of apertures along an axis extending transversely to said first direction after application of said shearing force than before.

42. An interlocking device according to claim 41, wherein said first portion and said second portion each has at least one surface that is electrically conductive and at least one surface that is electrically insulative.

43. An interlocking device according to claim 41, wherein said first plurality of islands is arranged as a two-dimensional array.

44. An interlocking device according to claim 41, wherein said structure includes a second plurality of islands.

45. An interlocking device according to claim 41, wherein said first plurality of islands and said second plurality of islands are hermaphroditic.

46. An interlocking device according to claim 41, wherein said first plurality of islands is arranged as a linear array.

47. An interlocking device according to claim 41, wherein ones of said first plurality of islands have a top surface, further wherein said top surface is configured so as to direct ones of said islands into approximate alignment with ones of said apertures when subjected to a relative compressive force acting in a direction generally perpendicular to said basal surface.

48. An interlocking device according to claim 47, wherein said first portion includes a plurality of first coupling members positioned on said basal surface, further wherein said top surfaces and said plurality of first coupling members are designed so that continued application of said relative compressive force after said top surface meets said plurality of first coupling members causes said ones of said first plurality of islands to move laterally so as to effect said relative shearing motion.

49. An interlocking device according to claim 41, wherein said plurality of apertures and said first plurality of islands are arranged in a two dimensional array, said first plurality of islands and said plurality of apertures being configured so as to allow said relative sliding engagement as a result of application of said relative shearing force in a first direction normal to said basal surface, and said first plurality of islands and said plurality of apertures being configured so as to allow said sliding engagement as a result of application of a different relative shearing force in a second direction normal to said basal surface.

50. An interlocking device according to claim 49, wherein said first plurality of islands and said plurality of apertures are configured so as to allow said first portion to maintain engagement with said second portion when said relative shearing force in said first direction is shifted to said different relative shearing force in said second direction such that said greater force is required to remove said first plurality of islands from said plurality of apertures after application of said different relative shearing force.

51. An interlocking device comprising:
  a. a first portion having a plurality of apertures and X, Y, and Z coordinates, each of said apertures having a chevron configuration defined by first and second sidewalls that extend transversely to said X, Y, and Z coordinates;
  b. a second portion having a first edge, a first plurality of islands and mutually orthogonal X, Y, and Z coordinates, each of said first plurality of islands terminating adjacent said first edge and having third and fourth sidewalls that extend transversely to said X, Y and Z axes;
  c. a third portion having a second edge, a second plurality of islands and mutually orthogonal X, Y, and Z coordinates, each of said second plurality of islands terminating adjacent said second edge and having fifth and sixth sidewalls that extend transversely to said X, Y, and Z axes;
  d. wherein said islands in said second and third portions are configured and positioned so that when said first and second edges are moved into confronting relation, each of said islands in said second portion is adjacent a corresponding respective island in said third portion forming an island pair, each of said island pairs to be received in a corresponding respective one of said plurality of apertures; and
  e. wherein said first, second, third fourth, fifth, and sixth sidewalls are formed so that when said island pairs are received in said apertures, said first sidewalls engage said third and fifth sidewalls and said second sidewalls engage said fourth and sixth sidewalls so as to resist separation of said first portion from said second and third portions.

52. An interlocking device comprising:
  a. a first portion having an aperture and first, second and third sidewalls that define said aperture, said first and second sidewalls forming an acute angle with said third sidewall and converging, as measured along an axis extending parallel to said first surface, further wherein said third sidewall includes a first locking member:
  b. a second portion having fourth, fifth, and sixth sidewalls, said second portion being sized and shaped for receipt in said aperture such that said fourth and fifth sidewalls engage said first and second sidewalls, respectively, and said third and sixth sidewalls confront one another:
  c. further wherein said sixth sidewall includes a second locking member designed to lock with said first locking member so as to restrict relative movement of said first and second portions when said second portion is received in said aperture.

53. An interlocking device according to claim 52, further comprising a third portion having an aperture sized to receive said first portion with a locking fit.

54. An interlocking device according to claim 52, wherein said second portion includes an edge and said first locking member is a moveable latch and said second locking member is said edge.

55. An interlocking device according to claim 52, wherein one of said first and second locking members has a recess and the other has a projection.

56. An interlocking device comprising:
  a. a first portion having an aperture and first, second and third sidewalls that define said aperture, said first and second sidewalls forming an acute angle with said third sidewall and converging as measured along an axis extending parallel to said third wall, further wherein said first portion includes a moveable locking member;
  b. a second portion having fourth, fifth, and sixth sidewalls and an edge, said second portion being sized and shaped for receipt in said aperture such that said fourth and fifth sidewalls engage said first and second sidewalls, respectively, and said third and sixth sidewalls confront one another;
  c. further wherein said locking member is designed and positioned to engage said edge of second portion when said second portion is inserted in said aperture so that said locking member restricts said second portion from exiting said aperture in a first direction extending parallel to said third sidewall.

57. An interlocking device according to claim 56, wherein said first portion and said second portion each has at least one surface that is electrically conductive and at least one surface that is electrically insulative.

58. An interlocking device according to claim 56, wherein said locking member is constructed to move between a first position, during insertion of said second portion into said aperture, and a second position, wherein said locking member engages said edge.

59. An interlocking device according to claim 56, wherein said first, second, fourth, and fifth sidewalls are configured, and said second portion is sized, so as to cause said first and second portions to contact in a manner that restricts said second portion from exiting said aperture other than in said first direction.

60. An interlocking device according to claim 56, further comprising
  d. a first piece of material attached to said first portion; and
  e. a second piece of material attached to said second portion.

61. An interlocking device according to claim 60, wherein said first and second pieces of material are fabric.

* * * * *